US008461204B2

(12) United States Patent
Stock et al.

(10) Patent No.: US 8,461,204 B2
(45) Date of Patent: Jun. 11, 2013

(54) CYSTEINYL COMPOUNDS, COMPOSITIONS AND METHODS OF USE

(75) Inventors: Jeffry B. Stock, Princeton, NJ (US);
Maxwell Stock, Rocky Hill, NJ (US);
Keshava Rapole, Edison, NJ (US);
Seung-Yub Lee, Princeton, NJ (US);
Michael Voronkov, Pennington, NJ (US); Eduardo Perez, Somerset, NJ (US); Joel Gordon, Princeton Junction, NJ (US); Shuyi Chen, Somerset, NJ (US)

(73) Assignee: Signum Biosciences, Inc., Monmouth Junction, NJ (US)

( * ) Notice: Subject to any disclaimer, the term of this patent is extended or adjusted under 35 U.S.C. 154(b) by 0 days.

(21) Appl. No.: 13/566,839

(22) Filed: Aug. 3, 2012

(65) Prior Publication Data

US 2012/0328540 A1    Dec. 27, 2012

Related U.S. Application Data

(63) Continuation-in-part of application No. 12/616,781, filed on Nov. 12, 2009, now Pat. No. 8,372,884, and a continuation-in-part of application No. 12/690,906, filed on Jan. 20, 2010, and a continuation-in-part of application No. 12/945,813, filed on Nov. 12, 2010.

(60) Provisional application No. 61/113,498, filed on Nov. 11, 2008, provisional application No. 61/145,887, filed on Jan. 20, 2009, provisional application No. 61/260,401, filed on Nov. 12, 2009.

(51) Int. Cl.
*A61K 31/198* (2006.01)
*C07C 323/24* (2006.01)
*A61K 31/197* (2006.01)
*C07C 323/59* (2006.01)

(52) U.S. Cl.
CPC ............. *A61K 31/197* (2013.01); *C07C 323/59* (2013.01)
USPC .......................................... 514/562; 562/557

(58) Field of Classification Search
CPC ............................ A61K 31/197; C07C 323/59
USPC ........................................... 514/562; 562/557
See application file for complete search history.

(56) References Cited

U.S. PATENT DOCUMENTS

| 5,043,268 | A  | 8/1991  | Stock          |
| 5,202,456 | A  | 4/1993  | Rando          |
| 5,491,164 | A  | 2/1996  | deSolms et al. |
| 5,571,687 | A  | 11/1996 | Casey et al.   |
| 5,965,539 | A  | 10/1999 | Sebti et al.   |
| 6,251,882 | B1 | 6/2001  | Uckun et al.   |
| 7,745,589 | B1 | 6/2010  | Spielmann et al. |
| 2007/0004803 | A1 | 1/2007 | Gibbs et al.   |
| 2009/0192332 | A1 | 7/2009 | Rapole et al.  |

FOREIGN PATENT DOCUMENTS

| WO | 2006135894 A1 | 12/2006 |
| WO | 2010056778 A1 | 5/2010 |
| WO | 2010090845 A1 | 8/2010 |

OTHER PUBLICATIONS

Dugan et al, Biology of Reproduction, Changes in Protein Prenylation and Prenyltransferase Activity in the Rat Seminiferous Epithelium During Early Stages of Spermatogenesis, 1995, 53, pp. 958-973.*
Winter-Vann et al, Nature, Post-prenylation-processing Enzymes as New Targets in Oncogenesis,May 2005, vol. 5, pp. 405-412.*
International Search Report for International Application No. PCT/US2009/064077 dated Jan. 15, 2010.
Written Opinion of the International Search Authority for International Application No. PCT/US2009/064077 dated Jan. 15, 2010.
International Preliminary Report on Patentability for International Application No. PCT/US2009/064077 dated May 17, 2011.
International Search Report for International Application No. PCT/US2010/021544 dated Jun. 16, 2010.
Written Opinion of the International Search Authority for International Application No. PCT/US2010/021544 dated Jun. 16, 2010.
International Preliminary Report on Patentability for International Application No. PCT/US2010/021544 dated Jul. 26, 2011.
Tan et al.; "Identifying the Recognition Unit for G Protein Methylation"; The Journal of Biological Chemistry; Dec. 21, 1990; vol. 266, No. 17; pp. 10719-10722.
Perez-Sala; "Protein Isoprenylation in biology and disease: general overview and perspectives from studies with genetically engineered animals"; Frontiers in Bioscience 12; May 1, 2007; pp. 4456-4472.
Perry et al.; "Cysteine Chloromethyl and Diazomethyl Ketone Derivatives with Potent Anti-Leukemic Activity"; Bioorganic & Medical Chemistry Letters 10; (2000); pp. 547-549.
Pillinger et al.; "Characterization of a Plasma Membrane-associated Prenylcysteine-directed α Carboxyl Methyltransferase in Human Neutrophils"; The Journal of Biological Chemistry; vol. 269, No. 2; 1994; pp. 1486-1492.
Desrosiers et al.; "Modulation of Rho and Cytoskeletal Protein Attachment to Membranes by a Prenylcysteine Analog"; The Journal of Biological Chemistry; vol. 275, No. 20; 2000; pp. 14949-14957.

* cited by examiner

*Primary Examiner* — Paul A Zucker
(74) *Attorney, Agent, or Firm* — SorinRand LLP

(57) ABSTRACT

Among other things, the present invention provides novel compounds capable of effectively inhibiting inflammatory responses that are mediated by G-proteins or GPCRs in neutrophils, macrophages and platelets. In particular, the compounds of the present invention act as inhibitors of edema, inhibitors of erythema and inhibitors of MPO (myeloperoxidase), pharmaceutical compositions containing the same compounds and the use thereof for the treatment of diseases that may benefit from edema, erythema and MPO inhibition, such as inflammation (acute or chronic), asthma, autoimmune diseases, and chronic obstructive pulmonary disease (COPD) (e.g., emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Chron's disease and ulcerative colitis, etc.), and central nervous system disorders (e.g., Parkinson's disease).

12 Claims, 3 Drawing Sheets

Figure 1

| Compound Number | Structure | % Inhibition | | | Dose |
|---|---|---|---|---|---|
| | | Edema | MPO | Erythema | |
| A | 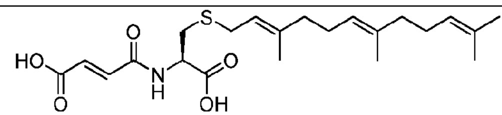 | 58.18 ± 13.02 | 78.39 ± 9.71 | 41.1 ± 13.84 | 0.2 mg/20 µL |
| | | 77.52 ± 10.21 | 93.24 ± 1.3 | - | 0.8 mg/20 µL |
| B | 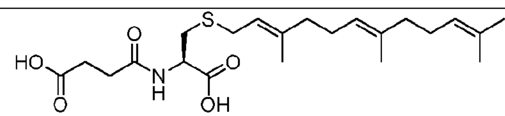 | 42.56 ± 5.86 | 53.91 ± 2.02 | - | 0.2 mg/20 µL |
| | | 61.13 ± 16.31 | 82.78 ± 7.91 | - | 0.8 mg/20 µL |
| AFC | 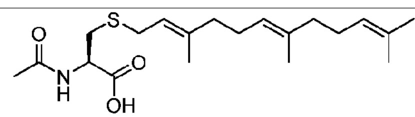 | (-)2.574 ± 19.68 | 2.025 ± 25.49 | (-)6.87 ± 7.37 | 0.2 mg/20 µL |
| | | 37.58 ± 5.57 | 66.42 ± 5.65 | 31.95 ± 15.14 | 0.8 mg/20 mL |

Figure 2

| Compound | Structure | M.W. | ED$_{50}$ value (mg/ml) for Inhibitory Activity[a] | | |
|---|---|---|---|---|---|
| | | | Edema | Erythema | MPO |
| A | 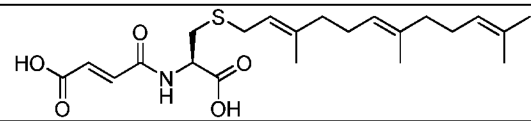 | 423.57 | 180 ± 11 | 109 ± 21 | 264 ± 12 |
| B | 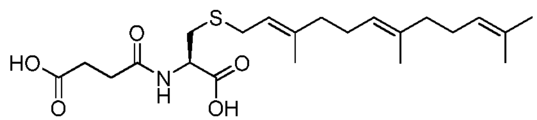 | 425.22 | 452 ± 11 | 106 ± 21 | 377 ± 12 |
| AFC | 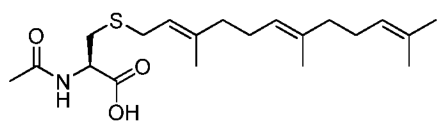 | 367.55 | 553 ± 20 | 109651 ± 54 | 1342 ± 349 |

[a] 5 concentrations were tested on the same day (1 concentration/6 mice). Compound A was tested in duplicate and AFC was tested in quadruplicate.

Figure 3.

| Compound | IC 50 (µg/mL) |
|---|---|
| BPO | 161.0 |
| AFC | 12.9 |
| Compound A | 134.8 |
| Compound B | 179.7 |

CYSTEINYL COMPOUNDS, COMPOSITIONS AND METHODS OF USE

CROSS-REFERENCE TO RELATED APPLICATIONS

This is a continuation-in-part of U.S. patent application, Ser. No. 12/616,781 filed Nov. 12, 2009, now U.S. Pat. No. 8,372,884, which claims priority from U.S. Provisional Patent Application, Ser. No. 61/113,498 filed Nov. 11, 2008. This is also a continuation-in-part of U.S. patent application, Ser. No. 12/690,906 filed Jan. 20, 2010, which claims priority from U.S. Provisional Patent Application, Ser. No. 61/145,887, filed Jan. 20, 2009. This is also a continuation-in-part of U.S. patent application, Ser. No. 12/945,813, filed Nov. 12, 2010, which claims priority from U.S. Provisional Patent Application, Ser. No. 61/260,401 filed Nov. 12, 2009. The entire disclosures of each of the aforementioned applications are incorporated herein by reference.

BACKGROUND

Inflammation often is a bodily response to infection or injury in which cells involved in detoxification and repair are mobilized to the compromised site by inflammatory mediators. The infection or injury can result from any of a variety of causes including acute or chronic disease, disorders or conditions; trauma, environmental conditions, or aging. For example, inflammation may result from diseases, disorders, syndromes, conditions and injuries of the cardiovascular, digestive, integumentary, muscular, nervous, reproductive, respiratory and urinary systems. Representative diseases, disorders or conditions that involve inflammation include atherosclerosis, irritable bowel syndrome, tendonitis, Alzheimer's disease and vascular dementia, multiple sclerosis, diabetes, endometriosis, asthma and kidney failure.

In addition, inflammation may result from diseases, disorders, syndromes, conditions and injuries of cartilage and tissue, including skin. Representative diseases, disorders or conditions involving inflammation of the skin include rosacea, psoriasis, acne, or the like, and include diseases, disorders or conditions which may be exacerbated by the presence or colonization of agents or vectors, such as bacteria.

Difficulties associated with the treatment of conditions related to bacterial colonization of mammalian epithelium are well-appreciated amongst dermatologists. This is particularly true in the case of skin and wound antisepsis, where the most effective treatment of epithelial conditions caused or aggravated by bacterial colonization, often includes the use of a topical anti-bacterial agent.

The emergence of bacterial resistance to commonly-used antibiotics, however, has posed an ever-increasing challenge in the treatment, prevention and containment of epithelial-related conditions, caused or aggravated by bacteria. There is a clear and urgent need for innovative and cost-effective methods for an efficacious treatment, prevention and/or management of such conditions.

Other background and methods may be found in U.S. Pat. Nos. 5,043,268, 5,202,456, 5,705,528; United States Patent Publications: 2005/0277694, 2007/0004803, 2009/0155186, 2009/0170917; World Publication WO 2009/102997, and U.S. Provisional Patent Application 61/113,498, disclosure of each of which is incorporated herein by reference.

N-acetyl-farnesyl-cysteine ("AFC"), also referred to as N-acetyl-5-trans, trans-farnesyl-L-cysteine, is a signal transduction modulator that has been shown to reduce inflammation in mice. AFC is a polyisoprenyl-protein inhibitor, and has been shown to be a competitive inhibitor of membrane-associated isoprenyl-5-cysteinyl methyltransferase. AFC has also been shown to block some neutrophil, macrophage, and platelet responses in vitro. Treatment of inflammatory diseases or disorders with traditional anti-inflammatory drugs, e.g., corticosteroids and non-steroidal anti-inflammatory drugs ("NSAIDS") can cause multiple side effects, e.g., appetite and weight gain, excess sweating, high blood pressure, nausea, vomiting, diarrhea, etc.

What is needed is a compound advantageously having high anti-inflammatory and/or antibacterial activity for use against a variety of diseases, disorders or conditions.

BRIEF SUMMARY OF THE INVENTION

Among other things, the present invention provides novel compounds, or complexes comprising those compounds, that modulate the G-protein signaling cascade. The present invention provides certain isoprenyl compounds that are structurally related to N-acetyl-5-farnesyl-L-cysteine ("AFC"), but which comprise a succinyl moiety in place of the acetyl group. The compounds of the subject invention are therefore N-succinyl-5-farnesyl-L-cysteines and are generally referred to as "succinyl-farnesyl-cysteines" or "SFC's."

The present invention demonstrates surprising and desirable characteristics of certain such compounds or complexes. For example, the present invention demonstrates that certain such compounds and/or complexes or compositions show surprising inhibition of edema, erythema and dermal neutrophil infiltration, as measured by inhibition of MPO (myeloperoxidase), when compared to AFC.

In some embodiments, compounds or complexes useful in the present invention exhibit anti-inflammatory activity and are therefore considered to be anti-inflammatory agents. In some further embodiments, compounds useful in the present invention exhibit anti-bacterial activity and are therefore considered to be anti-bacterial agents. The present invention, inter alia, also provides compounds or complexes, or compositions comprising those compounds or complexes which can kill, inactivate, decolonize and/or inhibit the growth of microbes, such as bacteria, on a surface.

In some embodiments, compounds useful in the present invention exhibit both anti-inflammatory as well as antibacterial activity.

In some embodiments, the present invention provides methods to treat, prevent or ameliorate the symptoms of epithelial-related conditions. In some embodiments, epithelial-related conditions include skin conditions. In some embodiments, skin conditions can include cellulitis; erysipelas; impetigo; ecthyma; cutaneous anthrax; necroticizing fasciitis; toe web infections; sycosis barbae; furuncles; carbuncles; Staphylococcal scalded skin syndrome; blistering distal dactylitis; acute paronychia; folliculitis; acne vulgaris; cutaneous diphtheria; erythrasma; bacterial colonization of open wounds (e.g., cuts, lesions, scrapes, burns, lacerations, chronic wounds, or infected animal bites.)

In some embodiments, epithelial-related conditions include ocular conditions. In some embodiments, ocular conditions include ocular rosacea, chronic blepharitis; endophthalmitis, ocular rosacea, ocular inflammatory disease, blepharitis, conjunctivitis or allergic conjunctivitis, corneal damage, corneal inflammation, corneal scarring, corneal damage or trauma, conjunctiva damage or trauma, diabetic retinopathy, dry eye or dry eye syndrome, tear production or tear quality dysfunction, iritis, keratitis, retinitis, scleritis, uveitis, and age-related macular degeneration, or the like.

In some embodiments, epithelial-related conditions include respiratory conditions. In some embodiments, epithelial-related conditions include nasal conditions.

In some embodiments, epithelial-related conditions include oral conditions. In some embodiments, oral conditions include gingivitis, dental caries, or the like.

In some embodiments, epithelial-related conditions include conditions of the external ear, for example, otitis media, or the like.

In some embodiments, epithelial-related conditions include genitourinary or vaginal conditions. In some embodiments, vaginal conditions include bacterial vaginosis; chanchroid; syphilis; donovanosis; gonorrhea; lymphogranuloma venereum; non-gonococcal urethritis; staphylococcal infection, In some embodiments, epithelial-related conditions include rectal conditions.

In some embodiments, bacteria that can be treated using a compound, complex, or composition according to the subject invention includes *Propionibacterium acnes*. In some embodiments, epithelial-related conditions may be associated with clinical indications (e.g., infection).

In some embodiments, methods of the present invention are useful in treating epithelial-related conditions in animals, including humans in need of treatment thereof.

The present invention also provides compositions containing compounds described herein, methods of preparing such compounds and/or compositions, and methods of using such compounds and/or compositions.

In certain embodiments, the present invention provides uses of provided compounds and/or compositions in the treatment of inflammation. In certain embodiments, the present invention provides uses of provided compounds and/or compositions in the treatment of diseases that may benefit from edema inhibition, erythema inhibition and/or MPO inhibition, such as treating or lessening the severity of inflammatory diseases or disorders selected from inflammation (acute or chronic), asthma, autoimmune diseases, and chronic obstructive pulmonary disease (COPD) (e.g., emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Chron's disease and ulcerative colitis, etc.), and central nervous system disorders (e.g., Parkinson's disease).

While the various aspects of the disclosure herein are illustrated through the use of AFC, it is an object of the present invention to extend the various embodiments described herein utilizing a cysteinyl compound or a composition comprising a cysteinyl compound, and preferably a cysteinyl compound comprising a succinyl moiety in place of the acetyl moiety. Various other compounds and/or compositions as described herein would be known to those skilled in the art made aware of this disclosure. Accordingly, as described more fully below, in the accompanying figures, examples and descriptions, a related object of this disclosure includes various compounds and/or compositions, the choice as to which can be determined as desirable for a specific end use application.

In some embodiments, the subject invention includes a compound having the formula:

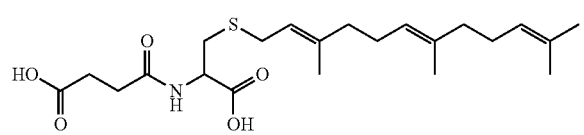 [SMILES: CC(C)=CCC/C(C)=C/CC/C(C)=C/CSCC(NC(=O)CCC(=O)O)C(=O)O]

referred to herein as Compound $B_0$.

In some embodiments, the subject invention comprises a compound having the formula:

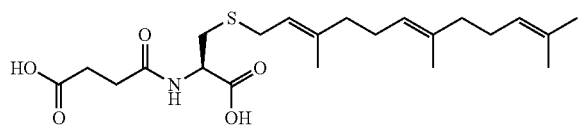 [SMILES: CC(C)=CCC/C(C)=C/CC/C(C)=C/CSC[C@H](NC(=O)CCC(=O)O)C(=O)O]

referred to herein as Compound B.

The compound can be complexed with a binding agent, such as a monosodium or disodium salt.

The compound can also be provided as a pharmaceutically acceptable composition, which is the compound formulated with a pharmaceutically acceptable adjuvant, carrier, or vehicle. The pharmaceutical composition can be formulated as an orally administered dosage form, an injectable formulation for parenteral administration or, preferably, can be formulated for topical administration.

Methods of using Compound B include treating or lessening the severity of a condition or disorder in a patient in need thereof comprising the step of administering to the patient, Compound B, a complex comprising Compound B, or a composition comprising the Compound B or its complex.

The conditions or disorders that can be treated by administration of Compound B, a complex comprising Compound B, or a composition comprising the Compound B or its complex, include an adnexa condition or disorder, e.g., alopecia.

Other conditions or disorders that can be treated with Compound B, a complex comprising Compound B, or a composition comprising the Compound B or its complex include conditions or disorders of the skin. One example of a skin condition or disorder that can be treated with Compound B, a complex comprising Compound B, or a composition comprising the Compound B or its complex is actinic keratosis.

A further condition or disorder that can be treated using Compound B, a complex comprising Compound B, or a composition comprising the Compound B or its complex is an inflammatory disease. Examples of such inflammatory diseases are irritant contact dermatitis, atopic dermatitis, seborrheic dermatitis, psoriasis, contact allergy, photosensitivity, contact urticaria, rosacea, cutaneous lupus, skin abrasion, bone and/or joint inflammation.

Additional conditions or disorders that can be treated using Compound B, a complex comprising Compound B, or a composition comprising the Compound B or its complex, is the inhibition or reduction of sensory irritation, itch, erythema, edema or vesiculation.

Disorders or conditions, including an epithelial condition, caused or aggravated by bacteria can be treated, or the severity can be lessened using Compound B, a complex comprising Compound B, or a composition comprising the Compound B or its complex. These conditions or disorders include cellulitis; erysipelas; impetigo; ecthyma e.g. ecthyma gangrenosum; hidradenitis; cutaneous anthrax; necroticizing fasciitis; toe web infections; sycosis barbae; furuncles and carbuncles; Staphylococcal scalded skin syndrome; blistering distal dactylitis; acute paronychia; folliculitis e.g. acne vulgaris; cutaneous diphtheria; erythrasma; bacterial colonization of open wounds e.g. cuts, lesions, scrapes, burns, lacerations, chronic wounds, or infected animal bites.

Treating or lessening the severity of epithelial conditions or disorders caused or aggravated by bacteria, such as acne vulgaris and rosacea, can be carried out using Compound B, a complex comprising Compound B, or a composition comprising the Compound B or its complex. The compounds, compositions or complexes of the subject invention can be effective against *Actinobacillus* sp., *Actinomyces* sp., *Bacillus* sp., *Bordatella* sp., *Branhamella* (*Moraxella*) sp., *Calymmatobacterium* sp., *Chlamydia* sp., *Chlamydophila* sp., *Corynebacterium* sp., *Eikenella* sp., *Enterobacter* sp., *Enterococcus* sp., *Escherichia* sp., *Fusobacterium* sp., *Haemophilus* sp., *Klebsiella* sp., *Mycobacterium* sp., *Nocardia* sp., *Pasteurella* sp., *Prevotella* sp., *Propionibacterium* sp. (including *Propionibacterium acnes*), *Proteus* sp., *Psuedomonas* sp., *Staphylococcus* sp., *Streptococcus* sp.

Compound B, a complex comprising Compound B, or a composition comprising the Compound B or its complex can also be useful for treating or lessening the severity of skin disorders or conditions caused by UV damage, such as photaging, and can be used in combination with a conventional sun-screening agent.

Definitions

"Activating Agent": As used herein, the term "activating agent" refers to a coupling agent. Exemplary activating agents include, but are not limited to: benzotriazol-1-yl-oxy-tris-(dimethylamino)-phosphonium hexafluorphosphate (BOP), N,N'-carbonyldiimidazole (CDI), N,N'-dicyclohhexylcarbodiimide (DCC), N,N'-diisopropylcarbodiimide (DIC), 3-(diethoxyphosphorylloxy)-1,2,3-benzotriazin-4-(3H)-one (DIC), 3-(diethoxyphosphorylloxy)-1,2,3-benzotriazin-4-(3H)-one (DEPBT), N-ethyl-N'-(3-dimethylaminopropyl)carbodiimide hydrochloride (EDC), 2-(1H-benzotriazol-1-yl)-1,1,3,3-tetramethyluronoium hexafluorphosphate (HBTU), 2-(3,4-dihydro-4-oxo-1,2,3-benzotriazin-3-yl)-N,N,N',N'-tetramethyluronium hexafluorophosphate (HDBTU), 2-(mercaptobenzothiazol)-N,N,N',N'-tetramethyluronium hexafluorophosphate (HMTU), 2-(endo-5-norbornene-2,3-dicarboxymido)-1,1,3,3-tetramethyluronium hexafluorophosphate (HNTU), 1-hydroxibenzotriazol monohydrate (HOBt*H2O), 1-hydroxy-1H-1,2,3-Triazole-4-carboxylate (HOCt), N-hydroxy-5-norbornene-2,3-dicarboxylimide (HONB), 3-hydroxy-3,4-dihydro-4-oxo-1,2,3-benzotriazine (HOOBt), S-(1-oxido-2-pyridyl)-thio-N,N,N',N'-tetramethyluronium hexafluorophosphate (HOTT), O-succinimidyl-1,3-dimethylpropyleneuronium hexafluorophosphate (HPD-OSu), S-(1-oxo-2-pyridyl)-thio-1,3-dimethylpropyleneuronium hexafluorophosphate (HPTDP), O-(1,2-dihydro-2-oxo-pyridyl]-N,N,N',N'-tetramethyluronium hexafluorophosphate (HPTU), 2-succinimido-1,1,3,3-tetramethyluronium hexafluorophosphate (HSTU), 4-(4,6-dimethoxy-1,3,5-triazin-2-yl)-4-morpholinium tetrafluoroborate (MMTM), 1-(mesitylene-2-sulfonyl)-3-nitro-1,2,4-triazole (MSNT), pentafluorphenol-tetramethyluronium hexafluorophosphate (PFTU), tris-n-propan-phosphonic acid anhydride (50% in AcOEt) (PPAA/AcOEt), tris-n-propan-phosphonic acid anhydride (50% in DMF) (PPAA/DMF), 2-(1H-benzotriazole-1-yl)-1,1,3,3-tetramethyluronium tetrafluoroborate (TBTU), N,N,N',N'-tetramethylchloroformamidinium-hexafluorophosphate (TCFH), N,N,N',N'-tetramethylfluoroformamidinium hexafluorophosphate (TFFH), 2-(endo-5-norbornene-2,3-dicarboxymido)-1,1,3,3-tetramethyluronium tetrafluoroborate (TNTU), S-(1-oxo-2-pyridyl)-thio-N,N,N',N'-tetramethyluronium tetrafluoroborate (TOTT), O-succinimidyl-1,3-dimethylpropyleneuronium tetrafluoroborate (TPD-OSu), S-(1-oxo-2-pyridyl)-thio-1,3-dimethylpropyleneuronium tetrafluoroborate (TPTDP), O-(1,2-dihydro-2-oxo-pyridyl]-N,N,N',N'-tetramethyluronium tetrafluoroborate (TPTU), or N,N,N',N'-tetramethyl-O-(succinimidyl)uronium tetrafluoroborate (TSTU).

"N-acetyl-farnesyl-5-cyteine compound" or an "AFC compound": As used herein, an "N-acetyl-farnesyl-5-cyteine compound" (or an "AFC compound"), as used herein, is a small molecule compound that is structurally related to AFC.

"Acyl": As used herein, the term "acyl" refers to a radical formed from an organic acid by removal of a hydroxyl group.

"Adnexa": The term "adnexa" means the appendages of an organ and, as used herein, refers to the adnexa or appendages of the skin, namely, the tissue or structures associated with or embedded in the skin such as hair and hair follicles, sweat glands, sebaceous glands and claws or nails. See also, "Skin Adnexa", defined below.

"Aliphatic": The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

"Alkenyl": As used herein, the term "alkenyl" denotes a monovalent group derived from a straight- or branched-chain hydrocarbon moiety containing at least one carbon-carbon double bond by removal of a single hydrogen atom. In certain embodiments, an alkenyl group employed in the invention contains 10-25 carbon atoms. In certain embodiments, an alkenyl group employed in the invention contains 10-20 carbon atoms. In certain embodiments, an alkenyl group employed contains 10 carbon atoms. In certain embodiments, an alkenyl group employed contains 15 carbon atoms. In certain embodiments, an alkenyl group employed contains 20 carbon atoms. Alkenyl groups include, for example, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, polyunsaturated alkenes including octadec-9,12-dienyl, octadec-9,12,15-trienyl, eicos-5,8,11,14-tetraenyl, farnesyl, geranyl, and geranylgeranyl, C-20 phytyl, and the like.

"Alkenylene": The term "alkenylene" refers to a bivalent alkenyl group. A substituted alkenylene chain is a polymethylene group containing at least one double bond in which one or more hydrogen atoms are replaced with a substituent. Suitable substituents include those described herein for a substituted aliphatic group.

"Alkyl": As used herein, the term "alkyl" means saturated, straight- or branched-chain hydrocarbon radicals derived from an aliphatic moiety containing between one and twenty-five carbon atoms by removal of a single hydrogen atom. In certain embodiments, an alkyl group employed in the invention contains 10-25 carbon atoms. In certain embodiments, an alkyl group employed in the invention contains 10-20 carbon atoms. In certain embodiments, an alkyl group employed contains 10 carbon atoms. In certain embodiments, an alkyl group employed contains 15 carbon atoms. In certain embodiments, an alkyl group employed contains 20 carbon atoms. In certain embodiments, an alkyl group employed in the invention contains 1-3 carbon atoms. In certain embodiments, an alkyl group employed contains 1-2 carbon atoms. In certain embodiments, an alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, and the like.

"Alkylamino": The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contains 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

"Alkylene": The term "alkylene" refers to a bivalent alkyl group. An "alkylene chain" is a polymethylene group, i.e., —(CH$_2$)$_n$—, wherein n is a positive integer, preferably from 1 to 6, from 1 to 5, from 1 to 4, from 1 to 3, from 1 to 2, from 2 to 3, or 3 to 4, 4 to 5, or 5 to 6. A substituted alkylene chain is a polymethylene group in which one or more methylene hydrogen atoms are replaced with a substituent. Suitable substituents include those described herein for a substituted aliphatic group.

"Alkynyl": As used herein, the term "alkynyl" denotes a monovalent group derived from a straight- or branched-chain hydrocarbon moiety containing at least one carbon-carbon triple bond by removal of a single hydrogen atom. In certain embodiments, an alkynyl group employed in the invention contains 10-25 carbon atoms. In certain embodiments, an alkynyl group employed in the invention contains 10-20 carbon atoms. In certain embodiments, an alkynyl group employed contains 10 carbon atoms. In certain embodiments, an alkynyl group employed contains 15 carbon atoms. In certain embodiments, an alkynyl group employed contains 20 carbon atoms. In certain embodiments, an alkynyl group employed in the invention contains 2-3 carbon atoms. In certain embodiments, an alkynyl group employed contains 2 carbon atoms. In certain embodiments, an alkynyl group employed contains 3 carbon atoms. Representative alkynyl groups include, but are not limited to, ethynyl, 2-propynyl (propargyl), 1-propynyl.

"Alkoxy", or "Alkythio": The term "alkoxy", or "alkylthio" as used herein refers to an alkyl group, as previously defined, attached to the parent molecule through an oxygen atom or through a sulfur atom. In certain embodiments, the alkyl, alkenyl, and alkynyl groups contain 1-20 aliphatic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

"Animal": The term animal, as used herein, refers to humans as well as nonhuman animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal. In some embodiments, the term animal is used to refer to veterinary animals (e.g., a bird, a horse, a cow, a primate, a dog, a cat, a mouse, a rodent or a pig).

"Anti-acne agent": As used herein, the term "anti-acne agent" refers to a group of chemical substances that when topically administered at the site of acne comedomes or microcomedomes, leads to a visible reduction of symptoms associated with the epithelial condition of acne vulgaris. Representative anti-acne agents include, for example, keratolytics, such as salicylic acid, sulfur, glycolic, pyruvic acid, resorcinol, and Nacetylcysteine; and retinoids such as retinoic acid and its derivatives (e.g., cis and trans, esters).

"Anti-bacterial agent": As used herein, the term "anti-bacterial agent" refers to an agent that inhibits the growth of a bacterium or kills a bacterium or results in bacterial decolonization of a surface. In some embodiments, the anti-bacterial agent can have bactericidal effect. In some embodiments, the anti-bacterial agent can have bacterostatic effect. In some embodiments, the anti-bacterial agent can have both bactericidal and bacterostatic effects. As used herein, the term "anti-bacterial agent" refers to both an antibacterial compound or pharmaceutically acceptable salts thereof.

"Antibiotic agent": As used herein, the term "antibiotic agent" means any of a group of chemical substances, isolated from natural sources or derived from antibiotic agents isolated from natural sources, having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefinetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, sulfonamides and fluoroquinolones.

"Antiseptic agent": As used herein, the term, "antiseptic agent" refers to a chemical agent that kills pathogenic or non-pathogenic bacteria. Antiseptic agents are sometimes referred to as "disinfectant agents", particularly when used to treat hard surfaces.

"Aryl" and "Heteroaryl": In general, the terms "aryl" and "heteroaryl" used alone or as part of a larger moiety as in "arylalkyl", "aryloxy", "heteroaryloxy" or "heteroarylalkyl" as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In some embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. The term "aryl" may be used interchangeably with the term "aryl ring." The term "heteroaryl" may be used interchangeably with the term "heteroaryl ring."

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO2; —CN; —CF3; —CH2CF3; —CHCl2; CH2OH; —CH2CH2OH; —CH2NH2; —CH2SO2CH3; —C(O)Rx; —CO2(Rx); —CON(Rx)2; —OC(O)Rx; —OCO2Rx; —OCON(Rx)2; —N(Rx)2; —S(O)2Rx; —NRx(CO)Rx, wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Binding partner": As used herein, the term "binding partner" refers to an agent that is non-covalently associated with an SFC compound in a complex as described herein. In some embodiments, the association between a binding partner and an SFC compound is stable in aqueous solution. In some embodiments, the association between a binding partner and an SFC compound is not stable in aqueous solution. In some embodiments, association between a binding partner and an SFC compound takes the form of a coordination complex. In some embodiments, the binding partner is a metal, a technetium isotope, a small molecule containing a basic nitrogen, a topical analgesic, an opiate, a morphinomimetic, an anticancer agent and/or an intraocular pressure reducing agent.

"Bivalent, branched or unbranched, saturated or unsaturated, $C_2$-$C_6$ (e.g., $C_2$, $C_3$, $C_4$, $C_5$, or $C_6$) hydrocarbon chain": As used herein, the term "bivalent, branched or unbranched, saturated or unsaturated, $C_2$-$C_6$ (e.g., $C_2$, $C_3$, $C_4$, $C_5$, or $C_6$) hydrocarbon chain", refers to bivalent alkylene, alkenylene, and alkynylene chains that are straight or branched as defined herein.

"Carrier": The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. In some embodiments, carriers are affirmatively beneficial (e.g., providing pharmaceutical and/or cosmetic benefits). In some embodiments, SFC acts as an acceptable carrier. In some embodiments, the term "carrier" when used in the pharmaceutical context (e.g., pharmaceutically acceptable carrier) means that an agent is present in a composition but does not abrogate the biological activity of another agent(s) present in a composition. In some embodiments, the term "carrier" when used in a cosmetic context (e.g., cosmetically acceptable carrier) means that an agent is present in a composition but does not but does not abrogate the biological activity and/or aesthetic effect of another agent(s) present in a composition. In some embodiments, a cosmetically acceptable carrier is used to topically administer cosmetics with which isoprenyl compounds of the present invention will remain stable and bioavailable. It will be understood that "cosmetically acceptable carriers" and "carriers" as defined herein are similar, if not often identical, in nature. In some embodiments, the term "carrier" when used in a cosmeceutical context (e.g., cosmeceutical carrier) means that an agent is present in a composition but does not abrogate the biological activity and aesthetic effect of another agent(s) present in a composition.

"Cysteinyl compound": As used herein, a "cysteinyl compound" is a small molecule compound that is structurally related to N-acetyl-5-farnesyl-L-cysteine (AFC) and has the following structure:

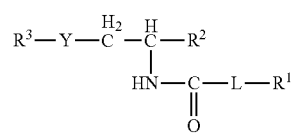

wherein L, $R^1$, $R^2$, $R^3$, and Y are as defined herein.

"Demulcent": As used herein, the term "demulcent" is an agent used to primarily alleviate irritation, particularly mucous membranes or abraded tissues. Exemplary demulcents include acacia, agar, alginates, mucilages, benzoin, carbomer, gelatin, glycerin, gums, hydroxyethyl cellulose, hydroxypropyl cellulose, hydroxypropyl methylcellulose, hydrogels, dextrins, starches, certain sugars, and polymeric polyhydric glycols, propylene glycol, sodium alginate, tragacanth, and combinations thereof.

"Decolonization": As used herein, the term "decolonization" refers to the reduction in the number of bacteria present in or on a tissue, such as on the surface of skin, that do not necessarily cause immediate clinical symptoms.

"Dialkylamino": The term "dialkylamino" refers to a group having the structure —NRR', wherein R and R' are each an aliphatic group, as defined herein. R and R' may be the same or different in a dialkylamino moiety. In certain embodiments, the aliphatic group contains 1-20 aliphatic carbon atoms. In certain other embodiments, the aliphatic group contains 1-10 aliphatic carbon atoms. In yet other embodiments, the aliphatic groups employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

"Effective amount": In general, the "effective amount" of an active agent (e.g., a therapeutic agent, composition, and/or formulation) refers to an amount sufficient to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, a therapeutically effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect. In some embodiments, the term "effective amount" when used in a cosmetic context (e.g., cosmetically effective amount) means that an agent is present in an amount sufficient to achieve an aesthetic effect. In some embodiments, the term "effective amount" when used in a cosmeceutical context (e.g., cosmeceutically effective amount) means that an agent is present in an amount sufficient to achieve a therapeutic and/or aesthetic effect.

"G-protein mediated condition": The term "G-protein mediated condition", as used herein means any disease or other deleterious condition for which the appearance, incidence, and/or severity of one or more symptoms correlates with changes in a G-protein signaling cascade. In some embodiments, one or more symptoms of the disease or condition is caused by a defect or alteration in G-protein signaling.

"Heteroaliphatic": The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In some embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO2; —CN; —CF3; —CH2CF3; —CHCl2; CH2OH; —CH2CH2OH; —CH2NH2; —CH2SO2CH3; —C(O)Rx; —CO2(Rx); —CON(Rx)2; —OC(O)Rx; —OCO2Rx; —OCON(Rx)2; —N(Rx)2; —S(O)2Rx; —NRx(CO)Rx, wherein each occurrence of Rx independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments described herein.

"Heteroatom": As used herein, the term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NRx (as in N-substituted pyrrolidinyl)).

"Heterocycle" or "Heterocyclyl": As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four heteroatoms independently selected from nitrogen, oxygen, or sulfur. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NRx (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. In certain embodiments, one or more carbon atoms may be substituted with an oxo group in the heterocyclyl ring. Examples of such groups include, without limitation, an isoindolin-1,3-dione moiety or a isoindolin-1, 3-dione moiety. A heterocyclyl group may be mono- or bicyclic. The term "heterocyclylalkyl" refers to an alkyl group substituted by a heterocyclyl, wherein the alkyl and heterocyclyl portions independently are optionally substituted.

"Hydrocarbon": The term "hydrocarbon", as used herein, refers to any chemical group comprising hydrogen and carbon. In some embodiments, a hydrocarbon consists of hydrogen and carbon. A hydrocarbon may be substituted or unsubstituted. The hydrocarbon may be unsaturated, saturated, branched, unbranched, cyclic, or polycyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. As used herein, a "bivalent hydrocarbon" refers to alkylene, alkenylene, or alkynylene, etc.

"In combination": As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered the same time, or in the same composition. Rather, so long as both (or more) agents remain in the subject's body, they are considered to be administered "in combination". Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

"Independently selected": The term "independently selected" is used herein to indicate that the R groups can be identical or different.

"Keratolytics": As used herein, "keratolytics" (desquamating agents) act to remove outer layers of the stratum corneum. This is particularly useful in hyperkeratotic areas. The keratolytics include benzoyl peroxide, fluorouracil, resorcinol, salicylic acid, tretinoin, and the like.

"Modulate": The term "modulate" refers to change in a parameter (e.g., a change in a binding interaction or an activity, etc.). Modulation can refer to an increase or a decrease in the parameter (e.g., an increase or decrease in binding, an increase or decrease in activity, etc.).

"Modulator": The term "modulator" refers to an agent that alters level and/or activity of its target (e.g., in the GPCR signal transduction pathway). In some embodiments, a modulator alters interaction between a protein in the GPCR signal transduction pathway and one or more other entities. In some embodiments, a modulator alters interaction between a modulator alters interaction between a protein in the GPCR signal transduction pathway and a substrate. Determination of whether an agent is a modulator can be performed directly or indirectly. Determination of whether an agent modulates an interaction can be performed directly, e.g., using an assay that detects the interaction between a protein in the GPCR signal transduction pathway and a substrate. Determination of whether an agent modulates an interaction can be performed with a technique that indirectly detects modulation, e.g., a technique that detects a biological activity that is downstream of, and dependent on, the protein-substrate interaction.

"Partially Unsaturated": As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Penetration enhancer" and "pharmaceutically acceptable penetration enhancer": The term "penetration enhancer" and "pharmaceutically acceptable penetration enhancer" as used herein is a non-toxic agent that improves bioavailability of a topical composition. In some embodiments, a penetration enhancer is known to accelerate the delivery of a substance through the skin (e.g., disrupting the barrier function of the skin without compromising its barrier effects on microorganisms and toxins). Typically, a penetration enhancer is selected to be non-toxic to skin of the intended recipient (e.g., human). A penetration enhancer is also desirably compatible with any pharmaceutically active agent with which it is administered. Representative penetration enhancers include, for example, and without limitation, such agents as 1-substituted azacycloheptane-2-ones (e.g., 1-n-dodecylcyclazacycloheptan-2-one, available under the trademark Azone® from Whitby Research Incorporated, Richmond, Va.), dipolar-aprotic solvents (e.g., N,N-dimethylacetamide ("DMA"), decylmethylsulfoxide ("C10 MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil. Additional penetration enhancers generally can be found in Remington: The Science and Practice of Pharmacy, 20th ed. (Gennaro, A. R., et al., eds.) Lippincott Williams & Wilkins: Philadelphia (2000), which is incorporated herein by reference.

"Pharmaceutically acceptable ester": The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In some embodiments, the esters are cleaved by enzymes such as esterases.

"Pharmaceutically acceptable prodrugs": The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Pharmaceutically acceptable salt": The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 66: 1-19, 1977; incorporated herein by reference. The salts can be prepared in situ during the final isolation and purification of the compounds of the invention, or separately, by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate, and aryl sulfonate.

"Preservative": As used herein, the term "preservative" has its art-understood meaning and refers to an agent that protects against undesirable chemical modifications of one or more components in a composition (e.g., protection against an undesirable chemical modification of an active ingredient). Suitable preservatives for use in the compositions of the present invention include, but are not limited to, one or more alkanols, disodium EDTA, EDTA salts, EDTA fatty acid conjugates, isothioazolinone, parabens such as methylparaben and propylparaben, polypropylene glycols, sorbates, urea derivatives such as diazolindinyl urea, or combinations thereof.

"Protecting group": One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p¬ methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t¬ butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-icyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(pmethoxyphenyl)phenylmethyl, tri (p-methoxyphenyl)methyl, 4-(4' bromophenacyloxyphenyl) diphenylmethyl, 4,4',4"-tris(4,5-dichlorophthalimidophenyl) methyl, 4,4',4"-tris(levulinoyloxyphenyl)methyl, 4,4',4"-tris (benzoyloxyphenyl)methyl, 3-(imidazol-1-yl)bis(4',4"-dimethoxyphenyl)methyl, 1,1bis(4-methoxyphenyl)-1'-pyrenylmethyl, 9-anthryl, 9-(9-phenyl)xanthenyl, 9-(9-phenyl-10oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), tbutyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloro acetate, trichloroacetate, trifluoroacetate, methoxyacetate, triphenylmethoxyacetate, phenoxyacetate, p-chlorophenoxyacetate, 3-phenylpropionate, 4oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o(dibromomethyl)benzoate, 2-formylbenzenesulfonate, 2-(methylthiomethoxy)ethyl, 4(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, mono succinoate, (E)-2-methyl-2-butenoate, o-(methoxycarbonyl)benzoate, α-naphthoate, nitrate, alkyl N,N,N',N' tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, pmethoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 14N,Ndimethylamino)ethylidene derivative, α-(N,N'-dimethylamino)benzylidene derivative, 2oxacyclopentylidene ortho ester, di-t-butylsilylene group (DTBS),1,3-(1,1,3,3tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1(1-adamantyl)-1-methylethyl carbamate (Adpoc), 1,1-dimethyl-2-haloethyl carbamate, 1,1 dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-tbutylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, pbromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(ptoluenesulfonyl)ethyl carbamate, [2(1,3-dithianyl)]methyl carbamate (Dmoc), 4-methylthiophenyl carbamate (Mtpc), 2,4-dimethylthiophenyl carbamate (Bmpc), 2phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(onitrophenyl)methyl carbamate, phenothiazinyl-(10)-carbonyl derivative, N'-ptoluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, pdecyloxybenzyl carbamate, 2,2-dimethoxycarbonylvinyl carbamate, o-(N,Ndimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1 methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(phydroxyphenyl)propanamide, 3-(o-nitrophenyl) propanamide, 2-methyl-2-(onitrophenoxy)propanamide, 2-methyl-2-(ophenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5 substituted 1,3-dimethyl-1,3,5-triazacyclohexan-2-one, 5-substituted 1,3-dibenzyl-1,3,5 triazacyclohexan-2-one, 1-substituted 3,5-dinitro-4-pyridone, N-methylamine, N-allyl amine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N' oxide, N-1,1-dimethylthiomethyleneamine, N-benzylideneamine, N-pmethoxybenzylideneamine, N-diphenylmethyleneamine, N-[(2pyridyl)mesityl]methyleneamine, N—(N',N'-dimethylaminomethylene)amine, N,N' isopropylidenediamine, N-p-nitrobenzylideneamine, N-salicylideneamine, N-5 chlorosalicylideneamine, N-(5-chloro-2-hydroxyphenyl]phenylmethylene amine, Ncyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitro amine, N-nitro so amine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracene-sulfonamide, 4-(4',8'-dimethoxynaphthylmethyl)benzene-sulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in Protective Groups in Organic Synthesis, Third Ed. Greene, T. W. and Wuts, P. G., Eds., John Wiley & Sons, New York: 1999, the entire contents of which are hereby incorporated by reference.

"Skin Adnexa": The term "skin adnexa" means the appendages of the skin and, as used herein, refers to the adnexa or appendages of the skin, namely, the tissue or structures associated with or embedded in the skin, such as hair and hair follicles, sweat glands, sebaceous glands and claws or nails. See also, "Adnexa", defined above.

"Skin Irritant": As used herein, the term "skin irritant" refers to a compound that, when applied to skin or a skin equivalents, elicits a cellular response characterized by the expression of an "irritant responsive gene." Examples of known skin irritants include, but are not limited to, sodium dodecyl sulfate ("SDS"), calcipotriol, and trans-retinoic acid. The term "skin irritant" is also intended to encompass unknown or suspected irritants, including but not limited to, those containing in some pharmaceuticals, cosmetics, and consumer products.

"Small Molecule": In general, as used herein, the term "small molecule" refers to an organic compound either synthesized in the laboratory or found in nature. Typically, a small molecule is characterized in that it contains several carbon-carbon bonds, and has a molecular weight of less than 1500, although this characterization is not intended to be limiting for the purposes of the present invention. Small molecules that act as binding agents as described herein are typically small molecules having a basic nitrogen moiety.

"Solubilizing agent": As used herein, the term "solubilizing agent" refers to a substance that enables solutes to dissolve. Representative examples of solubilizing agents that are usable in the context of the present invention include, without limitation, complex-forming solubilizers (e.g., citric acid, ethylenediamine-tetraacetate, sodium meta-phosphate, succinic acid, urea, cyclodextrin, polyvinylpyrrolidone, diethylammonium-ortho-benzoate, etc.), n-alkyl amine n-oxides, micelle-forming solubilizers (e.g., TWEEN®, including TWEEN 80®), organic solvents (e.g., acetone, phospholipids and cyclodextrins), polyoxamers, polyoxyethylene n-alkyl ethers, and polyoxyethylene sorbitan fatty acid ester.

"Stable": The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

"Substantially free of": As used herein, the term "substantially free of", when used to describe a material or compound, means that the material or compound lacks a significant or detectable amount of a designated substance. In some embodiments, the designated substance is present at a level not more than about 1%, 2%, 3%, 4% or 5% (w/w or v/v) of the material or compound. In some embodiments, the designated substance is present at a level below 1%, 0.9%, 0.8%, 0.7%, 0.6%, 0.5%, 0.4%, 0.3%, 0.2%, or 0.1%.

"Substituted": It will be appreciated that the compounds, as described herein, may be substituted with any number of substituents or functional moieties. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

"Surfactants": As used herein, the term "surfactant" is a surface-active substance, such as a detergent. Suitable surfactants for use with the inventive compositions include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. More particularly, an anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

"Sun screening agent": As used herein, the term "sun screening agent" refers to an agent that, when topically applied, absorbs or reflects some of the sun's ultraviolet radiation on skin exposed to sunlight, and therefore helps protect against sunburn. In some embodiments, a sun screening agent absorbed in the skin may lead to an increase in reactive oxygen species. Representative examples of sun screening agents usable in the present invention include, without limitation, p-aminobenzoic acid and its salts and derivatives thereof (p-dimethylaminobenzoic acid; ethyl, glyceryl, and isobutyl esters); anthranilates (i.e., o-aminobenzoates; benzyl, cyclohexenyl, linalyl, menthyl, methyl, phenyl, phenylethyl, and terpinyl esters); benzophenones (i.e., hydroxy- or methoxy-substituted benzophenones such as benzoresorcinol, butylmethoxydibenzoylmethane, 2,2'-dihydroxy-4,4'-dimethoxybenzophenone, etocrylene, 4-isopropyldibenzoylmethane, dioxybenzone, 3-4'-methylbenzylidene-boman-2-one, octabenzone, octocrylene, oxybenzene, sulisobenzone, and 2,2',4,4'-tetrahydroxybenzophenone); (butyl carbotol) (6-propyl piperonyl)ether; cinnamic acid derivatives (alpha.-phenyl cinnamonitrile; butyl cinnamoyl pyruvate; benzyl and methyl esters); diazoles (2-acetyl-3-bromoindazole, aryl benzothiazoles, methyl naphthoxazole, and phenyl benzoxazole); dibenzylacetone; dihydroxycinnamic acid derivatives (methylaceto-umbelliferone, methylumbelliferone, umbelliferone); di-hydroxynaphthoic acid and its salts; hydrocarbons (diphenylbutadiene, and stilbene); hydroquinone; o- and p-hydroxybiphenyldisulfona-tes; coumarin derivatives (3-phenyl, 7-hydroxy, and 7-methyl); naphtholsulfonates (sodium salts of 2-naphthol-3,6-disulfonic and of 2-naphthol-6, 8-disulfonic acids); quinine salts (bisulfate, chloride, oleate, sulfate and tannate); quinoline derivatives (8-hydroxyquinoline salts, and 2-phenylquinoline); salicylates (amyl, benzyl, di-propylene glycol, glyceryl, menthyl, octyl, and phenyl esters); tannic acid and its derivatives (e.g., hexaethylether); trihydroxy-cinnamic acid derivatives (daphnetin, daphnin, esculetin, esculin, methylesculetin; and the glucosides); and uric and violuric acids; and combinations thereof.

"Thio": The term "thio" used alone or as part of a larger moiety as in "alkylthio", "arylthio", "heteroalkylthio", or "heteroarylthio" refers to presence of a sulfur atom (e.g., as replacement of an oxygen). For example, "alkylthio" refers to an alkyl group, as previously defined, attached to the parent molecule through a sulfur atom. Similarly, "arylthio" refers to an aryl group, as previously defined, attached to the parent molecule through a sulfur atom.

"Treat," "treating" and "treatment": As used herein, the terms "treat," "treating" and "treatment," contemplate an action that occurs while a patient is suffering from the specified disease or disorder, which reduces the severity of the disease or disorder. Thus, "treat", "treating", and "treatment" refer to any type of treatment that imparts a benefit to a subject afflicted with a disease, including improvement in the condition of the subject (e.g., in one or more symptoms), delay in the progression of the disease, prevention or delay of the onset of the disease, etc.

"Unsaturated": The term "unsaturated", as used herein, means that a moiety has one or more units of unsaturation.

"Treat," "treating" and "treatment": As used herein, the terms "treat," "treating" and "treatment," contemplate an action that occurs while a patient is suffering from a specified disease, disorder or condition, which delays onset of and/or reduces the frequency or severity of one or more symptoms or features of the disease disorder or condition. Thus, "treat", "treating", and "treatment" refer to any type of treatment that imparts a benefit to a subject afflicted with a disease, disorder or condition, including improvement in the condition of the subject (e.g., in one or more symptoms), delay in the progression of the disease, disorder or condition, prevention or delay of the onset of the disease, disorder or condition.

BRIEF DESCRIPTION OF THE DRAWINGS

FIG. 1 depicts % inhibition determined from an edema assay, an erythema assay, and myeloperoxidase ("MPO") assay for Compound A, Compound B, and AFC.

FIG. 2 depicts $ED_{50}$ results (mg/mL) obtained for AFC, compound A and
Compound B using an edema assay, an erythema assay, and myeloperoxidase ("MPO") assay, as described.

FIG. 3 presents a table depicting the $IC_{50}$ results (µg/mL) obtained for Benzoyl Peroxide ("BPO"), AFC, and compounds of the invention, including Compound A and Compound B, demonstrating their respective anti-bacterial property.

DETAILED DESCRIPTION OF THE INVENTION

1. Description of Exemplary Compounds

As described above, the present invention provides cysteinyl compounds related in structure to AFC. AFC, and many cysteinyl compounds are characterized by an ability to reduce methylation of a protein having a carboxyl-terminal -CAAX motif, wherein C=cysteine, A=any aliphatic amino acid, and X=any amino acid. (See Rando, U.S. Pat. No. 5,202,456). The methylation reaction which is inhibited is part of a series of post-translational modifications involving the -CAAX motif. These modifications include polyisoprenylation of the cysteine of the -CAAX motif (on the sulfur), proteolysis of the carboxyl-terminal three amino acids (-AAX) and methylation of the carboxyl group of cysteine.

Compounds provided by the present invention include those described generally above, and are further illustrated by all classes, subclasses and species of each of these compounds disclosed herein.

According to one aspect, the present invention provides compounds of Formula I:

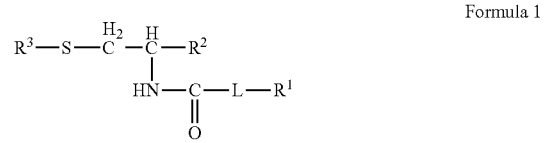

Formula 1 or a pharmaceutically acceptable salt thereof, wherein:

L is a bivalent, branched or unbranched, saturated or unsaturated, $C_2$-$C_6$ hydrocarbon chain wherein one or more methylene units of L is independently replaced by —O—, —S—, —NH—, —C(O)—, —C(=CH$_2$)—, or $C_3$-$C_6$ cycloalkylene, wherein L is optionally substituted by one or more groups selected from halogen, phenyl, an 8-10 membered bicyclic aryl ring, a 5-6 membered heteroaryl ring having 1-4 heteroatoms independently selected from nitrogen, oxygen, or sulfur, an 8-10 membered bicyclic heteroaryl ring having 1-4 heteroatoms independently selected from nitrogen, oxygen, or sulfur, or a 5- to 7-membered monocyclic or 7-10 membered bicyclic heterocyclyl ring having 1-2 heteroatoms independently selected from nitrogen, oxygen, or sulfur;

$R^1$ is hydrogen, —OH or —OR, wherein each R is independently hydrogen or an optionally substituted group selected from $C_{1-6}$ aliphatic or $C_{1-6}$ heteroaliphatic;

$R^2$ is —C(O)X, wherein X is independently R, —OR, a hydrogen, aryloxy, amino, alkylamino, dialkylamino, heteroaryloxy, hydrazine, a 6-10 membered aryl ring, a 5-6 membered heteroaryl ring having 1-4 heteroatoms independently selected from nitrogen, oxygen, or sulfur, wherein each R is independently hydrogen or an optionally substituted group selected from $C_{1-6}$ aliphatic or $C_{1-6}$ heteroaliphatic; and $R^3$ is a substituted or unsubstituted, branched or unbranched, saturated or unsaturated, $C_{10}$-$C_{25}$ aliphatic.

Examples of compounds of the present invention are set forth in Table $1_0$ below.

TABLE $1_0$

Exemplary Compounds

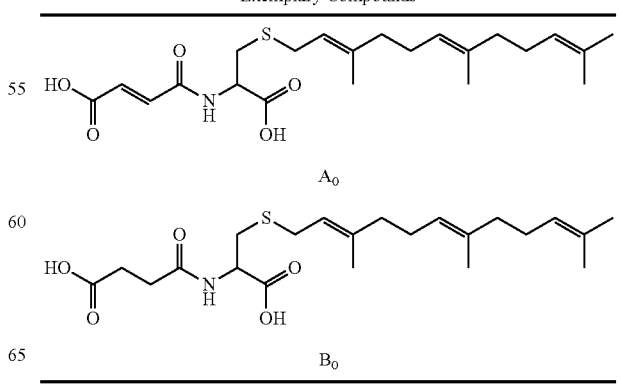

$A_0$ $B_0$

Exemplary preferred compounds of the present invention are set forth in Table 1 below.

TABLE 1

Exemplary Compounds

[Structure A: HO-C(=O)-CH=CH-C(=O)-NH-CH(C(=O)OH)-CH2-S-farnesyl]

A

[Structure B: HO-C(=O)-CH2-CH2-C(=O)-NH-CH(C(=O)OH)-CH2-S-farnesyl]

B

In certain embodiments, the present invention provides any compound depicted in Table 1, above, or a pharmaceutically acceptable salt thereof.

Compounds of formulae A and B may be provided according to the present invention in any of a variety of useful forms, for example as pharmaceutically acceptable salts, as particular crystal forms, etc. In some embodiments, prodrugs of one or more compounds of the invention are provided. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "Design and Application of Prodrugs", *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In some embodiments, the R groups can comprise one or more deuterium or tritium atoms. Mixtures of isomeric forms may be separated and/or purified by techniques as would be known to one skilled in this art, including but not limited to column chromatography.

In certain embodiments, provided compounds modulate a G-protein signaling cascade. In certain embodiments, provided compounds inhibit inflammation. In certain embodiments, activity of provided compounds may be characterized using a variety of in vivo or in vitro assays. For example, ability of provided compounds to inhibit inflammation may be assessed, for example, using assays that assess edema, erythema, and/or inhibition of myeloperoxidase ("MPO") as described herein.

In certain embodiments, provided compounds are considered to be inhibitors of inflammation when they show a percent inhibition in an edema assay of at least about 30, 35, 40, 50, 60, 70, 80, 90 or 95%, for example when provided at a dose 0.8 mg/20 pt. In certain embodiments, provided compounds are considered to be inhibitors of inflammation when they show a percent inhibition in an edema assay of at least about 5, 10, 15, 20, 25, 30, 35, 40, 50, 60, 70, or 80%, for example when provided at a dose of 0.2 mg/20 pt. In certain embodiments, provided compounds are considered to be inhibitors of inflammation when they result in an $ED_{50}$ in an edema assay of at least about 0.5, 1, 1.5, 2, 2.5, 3, 3.5, 4, 4.5-fold lower than that observed with vehicle alone.

In certain embodiments, provided compounds are considered to be inhibitors of inflammation when they show a percent inhibition in an erythema assay of at least about 25, 30, 35, 40, 50, 60, 70, 80, 90 or 95%, for example when provided at a dose of 0.8 mg/20 pt. In certain embodiments, provided compounds are considered to be inhibitors of inflammation when they show a percent inhibition in an erythema assay of at least about 5, 10, 15, 20, 25, 30, 35, 40, 50, 60, 70, 80, 90 or 95%, for example when provided at a dose of 0.2 mg/20 pt. In certain embodiments, provided compounds are considered to be inhibitors of inflammation when they result in an $ED_{50}$ in an erythema assay of at least about 0.5, 1, 1.5, 2, 2.5, 3, 3.5, 4, 4.5-fold lower than that observed with vehicle alone.

In certain embodiments, provided compounds are considered to be inhibitors of inflammation when they show a percent inhibition in an MPO assay of at least about 60, 70, 80, 90 or 95%, for example when provided at a dose of 0.8 mg/20 pt. In certain embodiments, provided compounds are considered to be inhibitors of inflammation when they show a percent inhibition in an MPO assay of at least about 5, 10, 15, 20, 25, 30, 35, 40, 50, 60, 70, or 80%, for example when provided at a dose of 0.2 mg/20 pt. In certain embodiments, provided compounds are considered to be inhibitors of inflammation when they result in an $ED_{50}$ in an MPO assay of at least about 0.5, 1, 1.5, 2, 2.5, 3, 3.5, 4, 4.5, 5, 5.5, 6 or 6.5-fold lower than that observed with AFC.

The present invention provides methods of preparing compounds provided herein. As will be appreciated by one of skill in the art, the synthetic methods described herein may be modified without departing from the scope of the present invention. For example, different starting materials and/or different reagents may be used in the inventive synthetic methods.

2. Methods of Synthesis

The present invention provides a process for preparing an N-substituted farnesyl cysteine analog with a terminal carboxylic acid. In certain embodiments, the inventive compounds are prepared as shown in the scheme below.

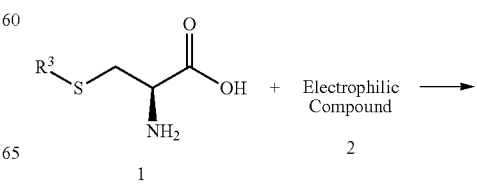

-continued

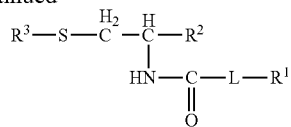

Formula I

To begin, a suitable compound 1 is reacted with a suitable electrophilic compound 2. In certain embodiments, the suitable compound 1 is S-trans, trans-farnesyl-L-cysteine. In certain embodiments, the electrophilic compound 2 is an anhydride. Exemplary anhydrides include succinic anhydride, maleic anhydride, 3-methylenedihydro-2,4-furandione, glutaric anhydride, N-phthaloyl-glutamic anhydride. In certain embodiments, the electrophilic compound 2 is an isocyanate. In certain embodiments, the isocyanate is ethyl-3-isocyanatopropionate. In certain embodiments, the electrophilic compound 2 is an activated ester of an acid. Exemplary activated esters of an acid include maleamic acid, mono-ethyl fumarate and BOC-glutamine. In certain embodiments, the electrophilic compound 2 is an acid chloride. Exemplary acid chlorides include adipoyl chloride, maleyl chloride, and sebacoyl chloride, etc. In certain embodiments, the electrophilic compound 2 is an activated acid. Exemplary activated acids include an acid that has been treated with an activating agent. One skilled in the art will be able to identify an appropriate activating agent from exemplary activating agents, including but not limited to the list as defined herein. The reaction is typically performed in the presence of a suitable base to form a compound of the subject invention. In certain embodiments, the base is $K_2CO_3$. The reaction is typically performed in a suitable solvent. In certain embodiments, the suitable solvent is a mixture of polar, aprotic solvents. In certain embodiments, whether used alone or as part of a mixture, the polar, aprotic solvents include DMF, DCM, NMP and THF.

In the above-described scheme and/or steps, the $R^1$, $R^2$, and $R^3$, groups of the various formulae are as described herein.

3. Compositions and Formulations

The present invention provides compositions comprising cysteinyl compounds as described herein. In certain embodiments, provided compositions contain additional components. In certain embodiments, all such additional components are pharmaceutically acceptable and the provided compositions are pharmaceutical compositions.

In certain embodiments, pharmaceutical compositions of the present invention comprise a cysteinyl compound, e.g., Compound A or Compound B, and a pharmaceutically acceptable carrier. A carrier in certain compositions according to the present invention may include liquid and, in particular may comprise a buffered, isotonic, aqueous solution. A carrier, including a pharmaceutically acceptable carrier, may be, or include, an excipient, such as a diluent, binder and the like, and or an additive, such as a stabilizing agent, preservative, solubilizing agent, and/or buffer as hereafter described.

4. Binding Partners

As mentioned above, a "binding partner" is an agent that is associated with an SFC compound in a complex as described herein.

In some embodiments, the binding partner can be a neutral, charged (i.e., in the form of an ion) or uncharged entity.

In certain embodiments, a binding partner is in the form of an ion.

In certain embodiments, a binding partner comprises a metal. In certain embodiments, the metal is selected from the group consisting of bismuth, cadmium, calcium, chromium, cobalt, copper, gold, iron, manganese, molybdenum, platinum scandium, silver, sodium, strontium, technetium, tin, titanium, vanadium, yttrium, zinc, and combinations thereof. In certain embodiments, the metal is a transition metal. In certain embodiments, the metal is strontium. In certain embodiments, the metal is calcium. In certain embodiments, the metal is sodium. In certain embodiments, the metal is zinc. In certain embodiments, the metal is titanium. In certain embodiments, the metal is silver.

In certain embodiments, a binding partner comprises a small molecule containing a basic nitrogen. In certain embodiments, the small molecule is glucosamine. In certain embodiments, the small molecule is nicotinamide. In certain embodiments, the small molecule is an NSAID. Exemplary NSAIDS include ampyrone, azapropazone, phenazone, piroxicam, droxicam, lornoxicam, tenoxicam and etoricoxib.

In certain embodiments, a binding partner comprises a topical analgesic. In certain embodiments, the topical analgesic may is selected from benzocaine, butamben, dibucaine, lidocaine, oxybuprocaine, pramoxine, proparacaine, proxymetacaine and tetracaine.

In certain embodiments, a binding partner comprises an opiate. Exemplary opiates include codeine, diamorphine, hydrocodone, morphine, naloxone, naltrexone, oxycodone, or pethidine.

In certain embodiments, a binding partner comprises a morphinomimetic. Exemplary morphinomimetics include meperidine and other phenylpiperidine derivatives (e.g., alfentanil, fentanyl, remifentanil, sufentanil, etc.).

In certain embodiments, a binding partner comprises an anti-cancer agent. Exemplary anti-cancer agents include camptothecin, irinotecan, lamellarin D, mitomycin, nitrogen mustards, temozolomide, topotecan, vinblastine, vincristine, vindesine, vinorelbine, etc.

In certain embodiments, a binding partner comprises an intraocular pressure reducing agent. Exemplary intraocular pressure reducing agents include brimonidine, timolol, etc.

In certain embodiments, a binding partner comprises a skin whitening agent. Exemplary skin whitening agents include hydroquinone, metronidazole, niacineamide (nicotineamide), etc. In certain embodiments, the skin whitening agent is niacineamide (nicotineamide).

In certain embodiments, a binding partner has anti-inflammatory activity. In certain embodiments, the SFC compound has anti-inflammatory activity. In certain embodiments, the SFC compound does not have anti-inflammatory activity. In certain embodiments, a provided complex shows anti-inflammatory activity that is comparable to or greater than that of the uncomplexed SFC compound. In certain embodiments, a provided complex shows anti-inflammatory activity that is comparable or greater than of the uncomplexed binding partner. In certain embodiments, a provided complex shows anti-inflammatory activity that is greater than the sum of the activities of the uncomplexed SFC compound and binding partner.

In certain embodiments, a binding partner has anti-microbial activity. In certain embodiments, the SFC compound has anti-microbial activity. In certain embodiments, the SFC compound does not have anti-microbial activity. In certain embodiments, a provided complex shows anti-microbial activity that is comparable to or greater than that of the uncomplexed SFC compound. In certain embodiments, a provided complex shows anti-microbial activity that is comparable or greater than of the uncomplexed binding partner. In certain embodiments, a provided complex shows anti-microbial activity that is greater than the sum of the activities of the uncomplexed SFC compound and binding partner.

In certain embodiments, a binding partner has sun-blocking activity. In certain embodiments, the SFC compound has sun-blocking activity. In certain embodiments, the SFC compound does not have sun-blocking activity. In certain embodiments, a provided complex shows sun-blocking activity that is comparable to or greater than that of the uncomplexed SFC compound. In certain embodiments, a provided complex shows sun-blocking activity that is comparable or greater than that of the uncomplexed binding partner. In certain embodiments, a provided complex shows sun-blocking activity that is greater than the sum of the activities of the uncomplexed SFC compound and binding partner.

5. Complexes

The present invention encompasses the finding that a complex comprising an SFC binding partner and a binding partner that is non-covalently associated thereto has desirable attributes, including for example, abilities to inhibit or reduce sensory irritation, MPO, erythema, edema and or vesiculation. In some embodiments, inventive complexes have inhibitory activity similar to or greater than that observed with the corresponding uncomplexed SFC compound; in some embodiments, inventive complexes have inhibitory activity similar to or greater than uncomplexed SFC.

In some embodiments, a provided complex has a solvent separated ion pair. In other embodiments, a provided complex does not have a solvent separated ion pair. In certain embodiments, a provided complex is a coordination complex. In some embodiments, a provided complex has d orbital involvement in the non-covalent interaction between compound and binding partner. In other embodiments, a provided complex does not exist as a solvent separated ion pair. In some embodiments, a provided binding partner is readily exchangeable with another binding partner. In other embodiments, a provided binding partner is not readily exchangeable with another binding partner. In some embodiments, a provided binding partner is monodentate or monovalent. In other embodiments, a provided binding partner is not monodentate or monovalent.

In certain embodiments, a provided complex is characterized by $^1$H NMR. In certain embodiments, a provided complex is characterized by one or more changes in chemical shift relative to the corresponding uncomplexed compound. In certain embodiments, a provided complex is characterized by line broadening relative to the corresponding uncomplexed compound. In certain embodiments, a provided complex is characterized by both line broadening relative to the corresponding uncomplexed compound, and by one or more changes in chemical shift relative to the corresponding uncomplexed compound.

In some embodiments, the binding partner and compound of the subject invention are present in a ratio within the range of about 0.5:4.5 to 2:1. In some embodiments, the binding partner and compound of the invention are present in a ratio of about 1:4. In some embodiments, the binding partner and compound of the invention are present in a ratio of about 1:1. In some embodiments, the binding partner and compound of the invention are present in a ratio of about 2:1. In some embodiments, the binding partner and compound of the invention are present in a ratio of about 1:2. In some embodiments, the binding partner and compound of the invention are present in a ratio of about 0.5:4.5. In some embodiments, the binding partner and compound of the invention are present in a ratio of about 1:3.

In some particular embodiments, when the binding partner is a metal, the binding partner and compound of the invention are present in a ratio of about 1:4. In certain such embodiments, the binding partner comprises strontium. In some particular embodiments, when the binding partner is a metal, the binding partner and compound of the invention are present in a ratio of about 2:1. In certain such embodiments, the binding partner comprises sodium.

In some particular embodiments, when the binding partner is a small molecule containing a basic nitrogen, the binding partner and compound of the invention are present in a ratio of about 1:1. In certain such embodiments, the binding partner comprises glucosamine. In certain other such embodiments, the binding partner comprises nicotinamide. In certain embodiments, when the ratio of binding partner and compound is 1:1, the binding partner comprises sodium.

In certain embodiments, the present invention provides complexes having the structural formula:

wherein:
  ∿∿ represents a non-covalent association;
  A represents a compound of the subject invention; and
  B represents a binding partner.

In certain embodiments, the present invention provides complexes having the structural formula:

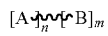

wherein:
  ∿∿ represents a non-covalent association;
  A represents a compound of the subject invention;
  B represents a binding partner;
  n represents an number in the range of 1 to 9, inclusive; and
  m represents an number in the range of 1 to 2, inclusive.

In certain embodiments, n is 4 and m is 1. In other embodiments, n is 1 and m is 1. In some embodiments, n is 2 and m is 1. In other embodiments, n is 1 and m is 2.

The present invention encompasses the surprising finding that certain complexes comprising a compound of the invention has unexpected desirable characteristics. For example, among other things, the present invention demonstrates that complexes comprising a compound of the invention with a strontium binding partner ("strontium complex") is surprisingly more effective at inhibiting inflammation than the complex comprising a compound of the subject invention with a calcium binding partner ("calcium complex"). In certain embodiments, it was found using an MPO Inhibition Protocol, the strontium complex had improved MPO inhibition than the calcium complex. In certain embodiments, it was found using an Edema Inhibition Protocol, that the strontium complex was more effective at decreasing edema than the calcium complex. In certain embodiments, the strontium complex is surprisingly more effective at decreasing sensory irritation than the calcium complex. In certain embodiments, the sensory irritation is pain.

The present invention provides systems for characterizing different complexes as described herein, and optionally for determining their relative activities and/or their activities in relationship to uncomplexed SFC compound and/or to SFC (see, for example, protocols and data presented in the Examples section).

In some embodiments, inventive complexes show anti-inflammatory activity that is at least as potent as that of uncomplexed SFC compound, uncomplexed binding partner, and/or or uncomplexed SFC. In some embodiments, inventive complexes show anti-inflammatory activity that it at least 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 25-fold 30-fold, 40-fold, 50-fold or more potent than the activity of uncomplexed SFC compound, uncomplexed binding partner, and/or or uncomplexed SFC.

The spectroscopic data indicates that in strontium, silver, and zinc complexes of SFC, the metal ion is in close proximity with all three polar moieties of the molecule: carboxylic acid, acetamide, and allylic sulfide. The changes in both chemical shift (2-15 ppm) and line broadening (1-5 Hz) of 13C signals adjacent to these moieties are consistent with multiple coordinative bonds between the metal ion and SFC. This finding is consistent with the strong affinity of amides and sulfur containing moieties to bind these and other metal ions, as known in the art. This finding is also consistent with the observed enhanced light and air stability of the SFC silver complex and its solutions, since it is known in the art that ordinary silver salts of carboxylic acids (e.g. silver acetate) are highly photosensitive and readily decompose to form insoluble silver oxide.

Compounds and complexes provided herein may be formulated into pharmaceutical compositions that include at least one provided compound of the present invention together with one or more pharmaceutically acceptable carriers, including excipients, such as diluents, binders and the like, and additives, such as stabilizing agents, preservatives, solubilizing agents, and buffers, as desired. Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a provided compound over a period of time. For example, gelatin, sodium carboxymethylcellulose and/or other cellulosic excipients may be included to provide time-release or slower-release formulations, especially for administration by subcutaneous and intramuscular injection.

In practical use, a provided compound of the present invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

If in an aqueous solution, a provided compound may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that provided compounds of the present invention may be in a dried and particulate form. In certain embodiments, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, provided compounds may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 p.m.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

Provided compounds of the present invention may be therapeutically administered by means of an injection, typically a deep intramuscular injection, such as in the gluteal or deltoid muscle, of a time release injectable formulation. In one embodiment, a provided compound of the present invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment, a provided compound of the present invention is formulated with a poly (ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany).

Such formulations may be made, for example, by combining a provided compound of the present invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated herein by reference. The formulation may be such that an injection is required on a weekly, monthly or other periodic basis, depending on the concentration and amount of a provided compound, the biodegradation rate of the polymer, and other factors known to those of skill in the art.

6. Uses

As described herein, the present invention relates to treating or lessening the severity of one or more diseases in which protein inhibitors that modulate the G-protein signaling cascade are known to play a role. Specifically, the present invention relates to a method of treating or lessening the severity of inflammatory diseases or disorders selected from inflammation (acute or chronic), inflammatory diseases or disorders (e.g., autoimmune diseases), inflammatory responses of the immune system (e.g., cutaneous lupus), skin diseases (e.g., rosacea, atopic dermatitis, seborrheic dermatitis, psoriasis, acne, actinic keratosis), hair follicle disorders (e.g. alopecia, including androgenic alopecia) wherein the method comprises administering to a patient in need thereof a composition of the present invention.

In certain embodiments, the provided compounds of the present invention are capable of effectively inhibiting inflammatory responses that are mediated by G-proteins or GPCRs in neutrophils, macrophages and platelets. Thus, provided compounds are inhibitors of edema, erythema and myeloperoxidase and are therefore useful for treating one or more disorders associated with inflammatory diseases or disorders as described herein. In particular, the present invention encompasses the finding that certain compounds having superior in vivo activity than other compounds in the same class. For example, relative to AFC, compound A has improved edema inhibition, improved erythema inhibition and improved MPO (myeloperoxidase) inhibition. Therefore, such compounds are administered to a subject suffering from or susceptible to one or more inflammatory diseases or disorders.

In certain embodiments, the treatment of inflammatory diseases or disorders is achieved using compounds without having the side effects of corticosteroids or NSAIDS.

In certain embodiments, such compounds are administered in vitro. In certain embodiments such compounds are administered in vivo.

Another aspect of the present invention is directed to methods of treating, preventing, or ameliorating inflammation by administering an effective amount of a provided compound.

In some embodiments, one or more inventive compounds, alone or together with one or more other pharmaceutically active agents, is used to whiten skin. In some such embodiments, the cysteinyl compound is applied topically.

In general, the actual quantity of provided compounds of the invention administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, an effective amount includes an amount of a provided compound (or mixture of provided compounds) or pharmaceutical composition of this invention that is sufficient to induce a desired effect, including specifically an anti-inflammation effect.

In general, the provided compounds of the present invention are highly active. For example, a provided compound can be administered at about 10 µg/kg to about 50 mg/kg body weight, depending on the specific provided compound selected, the desired therapeutic response, the route of administration, the formulation and other factors known to those of skill in the art. In some embodiments, the compounds can be administered from about 10-20 µg/kg, from about 20-30 µg/kg, from about 30-40 µg/kg, or about 40-50 µg/kg.

7. Uses of Complexes a. Skin Conditions

In some embodiments, provided herein is a method for treating, lessening the severity of and/or delaying onset of a skin condition, the method comprising the step of topically applying onto a surface of a subject, including a human, in need thereof, an effective amount of a composition comprising at least one complex as described herein, a carrier and optionally an additional active ingredient. In another aspect, provided herein is a method for treating, lessening the severity of and/or delaying onset of a skin condition, the method comprising the step of topically applying onto a surface of a subject, including a human, in need thereof, a provided complex. In a further embodiment, provided herein is a method of promoting healthy skin in a subject, including a human, in need thereof, the method comprising the step of topically applying onto a surface of a subject, including a human, in need thereof, an effective amount of a composition comprising at least one complex as described herein, a carrier and optionally an additional active ingredient. In a further aspect, provided herein is a method of promoting healthy skin in a subject, including a human, in need thereof, the method comprising the step of topically applying onto a surface of a subject, including a human, in need thereof, a provided complex.

In certain embodiments, the present invention provides for use of a provided complex in the manufacture of a medicament useful for treating a skin condition as described herein.

In some embodiments, the present invention provides a method for treating, lessening the severity of and/or delaying onset of inflammation in a subject, including a human, in need thereof, comprising the step of administering an effective amount of a composition comprising at least one complex as described herein, a carrier and optionally an additional active ingredient. In a further aspect, the present invention provides a method for treating, lessening the severity of and/or delaying onset of inflammation in a subject, including a human, in need thereof, comprising the step of administering a provided complex.

In certain embodiments, the present invention provides uses of provided complexes and/or compositions in the treatment or prevention of diseases, disorders, or conditions associated with suppression of inflammatory responses. In certain embodiments, the present invention provides a composition for treating or preventing conditions associated with suppression of the inflammatory responses in a subject, including a human, in need of treatment, that comprises of at least one complex as described herein, a carrier and optionally, an additional active ingredient. In some embodiments, provided herein is a method for treating, lessening the severity of and/or delaying onset of a disease, disorder, or condition associated with suppression of inflammatory responses in a subject, including a human, in need thereof, the method comprising the step of administering an effective amount of a composition comprising at least one complex as described herein, a carrier and optionally an additional active ingredient. In a further aspect, provided herein is a method for treating, lessening the severity of and/or delaying onset of a disease or condition associated with suppression of inflammatory responses in a subject, including a human, in need thereof, the method comprising the step of administering a provided complex.

Exemplary diseases, disorders or conditions that may be treated with provided complexes in accordance with the present invention are addressed individually below.

b. Rosacea

Rosacea is a chronic, inflammatory skin disorder that afflicts about 14 million people in the US (FoxAnalytics, The Dermatology Market Outlook to 2011, B.I. LTD, Editor: London, UK, p. 201; Crandall, M. A. Market Intelligence Report, K. Information, Editor, 2008: New York. p 359). With peak onset between the ages of 51 and 60, its incidence will grow substantially in the years ahead. The condition is characterized by a constellation of symptoms that include central facial erythema, telangiectasias, papules, granulomatous nodules, phyma formation and ocular changes. Flares and remissions occur without rationale. There are no known cures for rosacea. Exemplary cytokines associated with rosacea may include TNFα, ILβ, IL-6, IL-8, MCP-1 and Groα.

c. Psoriasis

Psoriasis is a chronic inflammatory skin disease affecting ~125 million people worldwide and approximately 2-3% of the general population in the US and Europe (Crandall, M. A. Market Intelligence Report, K. Information, Editor, 2008: New York. P. 359; Naldi, L., Curr. Drug Targets Inflamm. Allergy, 2004, 3: 121-128). Although the pathogenesis of psoriasis has not been fully elucidated, recent advances demonstrate targeting key mediators of inflammation as a promising therapeutic approach (Numerof et al., BioDrugs, 2006, 20: 93-103; Menter et al., J. Am. Acad. Dermatol., 2009, 60: 643-659). Direct therapeutic approaches include using antibodies or soluble receptors (i.e., biologics) to directly neutralize the specific cytokine of interest. However, biologic cytokine-derived therapies are expensive to produce, require sustained high blood levels in order to develop significant skin levels, may induce the production of neutralizing antibodies (leading to a diminished response to therapy), and must be administered by injection. Topical treatments have largely been ineffective, so market growth has been driven by systemic agents that have serious potential side effects. Corticosteroids remain the cornerstone of current topical treatment, but they are far from ideal. Long-term steroid use brings safety concerns ranging from issues of systemic absorption to cutaneous atrophy and its various clinical presentations. Today's US market for psoriasis treatments is greatly underserved, as only 60% of sufferers are being treated (Horn et al., J. Am. Acad. Dermatol. 2007, 57: 957-962).

Psoriasis can be conceived in simple terms, as a self reinforcing loop, in which deregulated inflammatory activity stimulates the epidermal Stat3c signaling pathway in the epidermis resulting in epidermal hyperplasia. The affected keratinocytes secrete cytokines which simulate the immune system, including T-helper cell (THc) infiltration and accumulation. Cytokines from the activated immune cells positively feedback on to the epidermal Stat3c pathway maintaining and amplifying the pathophysiology Inhibition of THc infiltration and accumulation would decrease Stat3c expression and the onset of psoriasis. Exemplary cytokines associated with psoriasis may include TNFα, IL1α, ILβ, IL-2, IL-6, IL-8, IL-12, MCP-1, Groα and IFNγ.

In some embodiments, the present invention provides methods of treating, lessening the severity of and/or delaying onset of inflammatory skin conditions such as psoriasis comprising administering to a subject in need thereof a dosage form comprising a provided complex, wherein cytokine levels and/or activity (e.g., levels and/or activity of one or more of TNFα, IL1α, ILβ, IL-2, IL-6, IL-8, IL-12, MCP-1, Groα and IFNγ) are reduced by more than about 20% as compared to levels and/or activity in a subject who has not been administered a provided complex (e.g., as determined using a K5.Stat3c psoriasis mouse model).

d. Atopic Dermatitis

Atopic dermatitis, or eczema, is characterized by chromic inflammation and irritation of the skin. Its causes are varied but immunological in nature. In the US, prevalence is 10% to 20% in children and 1% to 3% in adults. Topical dermatitis is caused by exposure to substances such as poison ivy, detergents and cosmetics that trigger allergic skin reactions. According to present theories, atopic dermatitis is thought to be caused by skin barrier defects that lead to increased exposure to substances such as allergens exposed by inhalation or ingestion. When dermatitis occurs, corticosteroids are the primary treatment. Atopic dermatitis, however, disproportionately affects children, and long-term steroid use in this population raises safety concerns. Exemplary cytokines associated with atopic dermatitis include but are not limited to TNFα, IL1β, IL-6, IL-8, MCP-1, Groα, IL-4, IL-5, IL-10, IL-13, IL-17 and IFNγ.

In some embodiments, the present invention provides methods of treating, lessening the severity of and/or delaying onset of inflammatory skin conditions such as atopic dermatitis comprising administering to a subject in need thereof a dosage form comprising a provided complex, wherein cytokine levels and/or activity (e.g., levels and/or activity of one or more of TNFα, IL1β, IL-6, IL-8, MCP-1, Groα, IL-4, IL-5, IL-10, IL-13, IL-17 and IFNγ) are reduced by more than about 20% as compared to levels and/or activity in a subject who has not been administered a provided complex (e.g., as determined using a ovalbumin-challenged ft/ft atopic dermatitis mouse model).

e. Seborrhic Dermatitis

Seborrheic dermatitis, commonly called dandruff, is a disease that causes redness, itchiness, and flaking of the skin. It affects the scalp, face, trunk, and particularly the sebum-gland rich areas of the skin, usually causing the skin to look inflamed and scaly.

Seborrheic dermatitis most often occurs in adults from 30 to 60 years of age and is more common in men than in women. Although the exact cause is not known, those afflicted with seborrhoeic dermatitis often have an unfavorable epidermic response caused by infections. Seborrheic dermatitis has also been linked to neurologic disorders such as Parkinson's disease and epilepsy. The treatment of seborrheic dermatitis depends on its location on the body. Treatment also depends on the person's age. Dandruff is often treated with a shampoo that contains salicylic acid, the prescription medicine selenium sulfide, zinc pyrithione, ketoconazole or coal tar. Steroid lotions may be used in adolescents and adults. Exemplary cytokines associated with seborrhic dermatitis include but are not limited to TNFα, ILβ, IL-6, IL-8, MCP-1, and Groα.

f. Inflammatory Cytokines and Rosacea, Psoriasis, Atopic Dermatitis and Seborrhic Dermatitis As described herein, the present invention provides methods of treating, lessening the severity of and/or delaying onset of inflammatory skin conditions (e.g., rosacea, psoriasis, atopic dermatitis and seborrhic dermatitis).

In some embodiments, the present invention provides methods of treating, lessening the severity of and/or delaying onset of inflammatory skin conditions (e.g., rosacea, psoriasis, atopic dermatitis and seborrhic dermatitis) by administering a provided complex or composition thereof. In certain embodiments, the present invention provides methods of treating, lessening the severity of and/or delaying onset of inflammatory skin conditions (e.g., rosacea, psoriasis, atopic dermatitis and seborrhic dermatitis) by administering a provided complex or composition thereof.

According to one aspect, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein inflammatory activity (e.g., MPO activity) is reduced by more than about 30% as compared to control (e.g., as determined using an MPO activity assay).

According to one aspect, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein inflammatory activity (e.g., MPO activity) is reduced by more than about 60% as compared to control (e.g., as determined using an MPO activity assay).

According to one aspect, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein inflammatory activity (e.g., erythema activity) is reduced by more than about 30% as compared to control (e.g., as determined using an erythema activity assay).

According to one aspect, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein inflammatory activity (e.g., edema activity) is reduced by more than about 30% as compared to control (e.g., as determined using an edema activity assay).

In some embodiments, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein cytokine levels and/or activity (e.g., levels and/or activity of one or more of TNF-$\alpha$, IL-1$\beta$, IL-8, IL-6, MCP-1, and Gro$\alpha$) are reduced by more than about 20% as compared to levels and/or activity in a subject who has not been administered said dosage form (e.g., as determined using a TPA-induced mouse ear inflammatory model).

In some embodiments, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein cytokine levels and/or activity (e.g., levels and/or activity of one or more of TNF-$\alpha$, IL-1$\beta$, IL-8, IL-6, MCP-1, and Gro$\alpha$) are reduced by more than about 20% as compared to levels and/or activity in a subject who has not been administered said dosage form (e.g., as determined using an LPS-TLR4-induced cytokine release inflammatory model in HMEC-1 cell line).

In some embodiments, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein cytokine levels and/or activity (e.g., levels and/or activity of one or more of TNF-$\alpha$, IL-1$\beta$, IL-8, IL-6, MCP-1, and Gro$\alpha$) are reduced by more than about 20% as compared to levels and/or activity in a subject who has not been administered said dosage form (e.g., as determined using an ATP$\gamma$S-purinergic receptor-induced cytokine release inflammatory model in HMEC-1 cell line).

In some embodiments, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein cytokine levels and/or activity (e.g., levels and/or activity of one or more of TNF-$\alpha$, IL-1$\beta$, IL-8, IL-6, MCP-1, and Gro$\alpha$) are reduced by more than about 20% as compared to levels and/or activity in a subject who has not been administered said dosage form (e.g., as determined using a TPA-induced cytokine release inflammatory model in NHEK cell line).

In some embodiments, the present invention provides methods of treating, lessening the severity of and/or delaying onset of inflammatory skin conditions (e.g., rosacea, psoriasis, atopic dermatitis and seborrhic dermatitis) comprising administering to a subject in need thereof a dosage form comprising a provided complex, wherein cytokine levels and/or activity (e.g., levels and/or activity of one or more of TNF-$\alpha$, IL-1$\beta$, IL-8, IL-6, MCP-1, and Gro$\alpha$) are reduced by more than about 20% as compared to levels and/or activity in a subject who has not been administered said dosage form (e.g., as determined using a TNF$\alpha$-induced cytokine release inflammatory model in HUVEC cell line).

g. Sun Screen (Protection from UV Damage)

Oxidative stresses caused by environmental insults such as ultraviolet ("UV") rays from the sun, chemical irritants, cigarette smoke exposure, consumption of foods with high saturated fat and environmental pollutants as well as the natural process of aging, contributing to the generation of free radicals and reactive oxygen species ("ROS"), stimulate inflammatory responses, especially in the skin (Pilla et al. Intl J. Cosm. Sci. 2005 v27 p 17-34). High levels of ROS contribute to adverse effects on the skin including erythema, edema, photoaging and skin cancer (Trouba et al. Antioxid. Redox Signal 2002 v4 p 665-673). Neutrophil infiltration during inflammatory responses is associated with increased oxygen consumption and generation of ROS. Extracellular inflammatory agonists such as fMLP bind to GPCRs such as formyl peptide receptors ("FPR"), to trigger the oxidative burst response (i.e., the rapid release of ROS). In some instances, sun screening agents absorbed into the skin lead to an increase in reactive oxygen species.

In certain embodiments, the present invention provides methods of treating, lessening the severity of and/or delaying onset of UV damage to especially the skin of a subject in need thereof, by administering a provided complex or composition thereof. According to one aspect, the present invention provides methods of treating, lessening the severity of and/or delaying onset of UV damage to especially the skin of a subject, in need thereof, comprising administering to a subject in need thereof a dosage form comprising a provided complex which inhibits more than about 20% of superoxide formation.

In certain embodiments, the present invention provides methods of decreasing the amount of reactive oxygen species in a cell, comprising the step of contacting the cell with a provided complex, wherein the complex inhibits more than about 20% of superoxide formation. In certain embodiments, the present invention provides methods of decreasing the amount of reactive oxygen species in a subject in need thereof, comprising the step of administering to the subject a provided complex, wherein the complex inhibits more than about 20% of superoxide formation.

In certain embodiments, the present invention provides for use of a provided complex in the manufacture of a sunscreening composition.

In certain embodiments, one or more provided complexes are used in combination with one or more conventional sunscreening agents. In certain embodiments, the present invention provides a method of using one or more provided complexes in combination with one or more conventional sunscreening agents, wherein the complex inhibits more than about 20% of superoxide formation.

h. Cosmetic Uses

Provided complexes may also be useful in the following: reducing fine lines and wrinkles, as anti-dandruff agents, in the treatment of skin disorders due to exposure to UV radiation, combating aging of the skin (e.g., light-induced or chronological aging), for delaying the onset of or repairing stretch marks, in treating or delaying the onset of alopecia of various origins, hair uses (e.g., hair relaxant, reducing irritation and/or inflammation of the scalp, adding natural shine, detangling, adding hair elasticity, hair moisturizer, restoring damaged, e.g, cysteine-depleted hair).

External insults such as pollution, UV radiation, chemical irritants, cigarette smoke, motor vehicle emissions, lotions, cosmetics, etc., cause an increase in the number of free radicals on the skin. Once formed, these highly reactive free radicals can enter the body and deplete electrons from healthy cells, causing inflammation. If left unchecked, increased free radicals could lead to the chronic inflammatory response that could likely cause skin aging, and contribute to premature appearance of fine lines and wrinkles. Provided complexes can protect the skin from UV damage, reverse skin aging and reduce the appearance of fine lines and wrinkles by targeting two key players in the aging process—free radicals, such as superoxide, and inflammation. In certain embodiments, the present invention provides a method of reducing fine lines and wrinkles on a subject in need thereof, comprising the step of administering to the subject a provided complex. In certain embodiments, the present invention provides a method of treating, lessening the severity of, or delaying the onset of a skin disorder caused by UV radiation in a subject in need thereof, comprising the step of administering to the subject a provided complex. In certain embodiments, the present invention provides a method of treating, lessening the severity of, or delaying the onset of aging of the skin in a subject in need thereof, comprising the step of administering to the subject a provided complex. In certain embodiments, the aging is light-induced. In certain embodiments, the aging is chronological aging.

Alopecia areata (AA) is a condition affecting humans, in which hair is lost from some or all areas of the body, usually from the scalp. AA affect .about.0.2% of the population and its incidence has been growing for the last few decades. AA is a T-cell mediated disease of the hair follicle. Predicted mechanisms of action include diversion of the T-cell response from the hair follicle to the epidermis, interference with lymphocyte homing, induction of nonspecific, localized immunosuppression as a result of a chronic immune response, and production of immunosuppressive cytokines (e.g. TGF-.beta. and IL-10). In certain embodiments, the present invention provides a method of treating, lessening the severity of, or delaying the onset of alopecia in a subject in need thereof, comprising the step of administering to the subject a provided complex.

Skin stretching creates inflammatory reactions, and inflammatory cells activate skin matrix degradation to form stretch marks. Down-regulation of pro-inflammatory cytokines, such as IL-1a, IL-1b, IL-8, and TNF-a, could repair, lessen the severity of, or delay onset of stretch marks. In certain embodiments, the present invention provides a method of repairing, lessening the severity of, or delaying the onset of stretch marks in a subject in need thereof, comprising the step of administering to the subject a provided complex.

Cysteine bonds are responsible for toughness and overall abrasion resistance of hair. The cysteine bond, also known as disulfide bond, is formed by cross-links between cysteine residues found in the main polypeptide chains that make up hair. Such disulfide bonds that are perpendicular to the axis of the hair and connect the polypeptide chains hold the hair fibers together and contribute to hair's toughness and abrasion resistance. The major metabolite of AFC compounds and complexes is farnesylated cysteine. Farnesylated cysteine can be used by the cellular machinery of hair follicles as a source of cysteine. Thus, AFC complexes may be used in the treatment of cysteine depleted hair such as damaged hair and split ends.

In some embodiments, the present invention provides a hair product comprising a provided complex. In certain embodiments, the hair product restores damaged hair. In certain embodiments, the hair product is hair relaxant. In certain embodiments, the hair product adds natural shine. In certain embodiments, the hair product is a detangler. In certain embodiments, the hair product adds hair elasticity. In certain embodiments, the hair product moisturizes the hair. In certain embodiments, the thinning hair is cysteine-depleted. In certain embodiments, the present invention provides a method of treating, lessening the severity of, or delaying the onset of irritation and/or inflammation of the scalp in a subject in need thereof, comprising the step of administering to the subject a provided complex. In certain embodiments, the present invention provides a method of treating, lessening the severity of, or delaying the onset of dandruff in a subject in need thereof, comprising the step of administering to the subject a provided complex.

Application of certain agents to hair such as, for example, hair relaxants, which commonly comprise basic agents (e.g., NaOH), can cause skin irritation (e.g., irritation and/or inflammation of the scalp). In some embodiments, one or more inventive complexes is/are administered together with such an agent (e.g., hair relaxant) to reduce skin irritation and/or inflammation.

8. Administration and Dosage Forms

Because of their ease of administration, tablets and capsules represent an advantageous oral unit dosage form. If desired, a composition including provided compound of the invention may be coated by standard aqueous or nonaqueous techniques. The amount of active compound, i.e. a cysteinyl compound of the present invention, in such therapeutically useful compositions is such that an effective dosage will be obtained. In another advantageous dosage unit form, sublingual pharmaceutical compositions may be employed, such as sheets, wafers, tablets or the like. An active compound can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Provided compounds of the present invention may also be administered parenterally.

Solutions or suspensions of these active peptides may be prepared in water suitably mixed with a surfactant, such as hydroxy-propylcellulose. Dispersions may also be prepared, such as dispersions in glycerol, liquid polyethylene glycols and mixtures thereof in oils. These preparations may optionally contain a preservative to prevent the growth of microorganisms. Lyophilized single unit formulations may also be utilized, which are reconstituted, such as with saline, immediately prior to administration, and thus do not require a preservative.

Pharmaceutical forms suitable for injectable use include, for example, sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and may be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Provided compounds of the invention of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which provided compounds of the invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

Compositions of the present invention may be in a form suitable for oral use, for example, as tablets, troches, lozenges, pills, aqueous or oily suspensions, solutions, dispersible powders or granules, emulsions, hard or soft capsules, syrups or elixirs, pastes, gels or the like.

Compositions intended for oral use may be prepared according to any known method, and such compositions may contain one or more excipients selected from the group consisting of sweetening agents, flavoring agents, coloring agents, and preserving agents in order to provide pharmaceutically elegant and palatable compositions. In general, the formulations for oral administration are prepared by uniformly and intimately admixing the active compound, i.e., a provided compound of the present invention or mixtures thereof, with a liquid or finely divided solid excipient, or both, and then, if necessary, shaping the resulting mixture.

A tablet may contain the active ingredient(s) in admixture with non-toxic pharmaceutically acceptable additives and/or excipients which are suitable for the manufacture of tablets. These additives or excipients may be, for example, fillers, wetting agents, inert diluents, such as calcium carbonate, sodium carbonate, lactose, calcium phosphate or sodium phosphate; granulating and noneffervescent disintegrating agents, for example, corn starch or alginic acid; binding agents, for example, starch, gelatin or acacia; and lubricating agents, for example, magnesium stearate, stearic acid or talc.

A tablet may be prepared by traditional methods such as by compressing or molding a powder or granules containing a provided compound. Compressed tablets may be prepared by compressing, in a suitable machine, the a provided compound in a free-flowing form, such as a powder or granules optionally mixed with a binder, lubricant, inert diluent, and/or surface active/dispersing agent(s). Molded tablets may be made by molding, in a suitable machine, a powdered provided compound moistened with an inert liquid binder.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled delivery. For example, a "delayed release" dosage form releases a product or substance at a time other than promptly after administration. Examples of delayed-release systems include repeat action tablets and capsules, and enteric coated tablets where timed release is achieved by a barrier coating.

Compositions of the present invention also may be formulated for oral use as hard gelatin capsules, where a provided compound is mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

In another embodiment, liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives.

The compositions of the present invention may be formulated as aqueous suspensions wherein a provided compound is in admixture with excipients additives and/or suitable for the manufacture of aqueous suspensions. Such additives and/or excipients are suspending agents, for example, sodium carboxymethylcellulose, methylcellulose, hydroxy propylmethylcellulose, sodium alginate, polyvinylpyrrolidone, gum tragacanth, and gum acacia; dispersing or wetting agents may be a naturally occurring phosphatide such as lecithin, or condensation products of an alkylene oxide with fatty acids, for example, polyoxyethylene stearate, or condensation products of ethylene oxide with long chain aliphatic alcohols, for example, heptadecaethyl eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending a provided compound in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral composition. These compositions may be preserved by the addition of an antioxidant such as ascorbic acid.

Compositions of the present invention may be formulated in the form of dispersible powders and granules suitable for composition of an aqueous suspension by the addition of water. Provided compound in such powders and granules is provided in admixture with a dispersing or wetting agent, suspending agent, and one or more preservatives. Suitable dispersing or wetting agents and suspending agents are exemplified by those already mentioned above. Additional excipients or example, sweetening, flavoring and coloring agents also may be present.

Compositions of the invention also may be in the form of oil in water emulsions. The oily phase may be a vegetable oil, for example, olive oil or arachis oil, or a mineral oil, for example a liquid paraffin, or a mixture thereof. Suitable emulsifying agents may be naturally occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Liquid based oral dosage forms, like their solid counterparts, usually contain at least 0.1 mg of a provided compound. One skilled in the art will be able to properly formulate a liquid formulation containing an appropriate amount of a provided compound per fluidic ounce, depending on the additive or carrier selected.

Formulations suitable for buccal administration include tablets and lozenges comprising a cysteinyl compound in a flavored base, such as sucrose, acacia or tragacanth; and pastilles comprising the cysteinyl compound in an inert base, such as gelatin and glycerin or sucrose and acacia.

Formulations of the present invention suitable for topical application to the skin take the form of an ointment, cream, lotion, paste, gel, spray, aerosol, or oil. Additives which may be used include petroleum jelly (e.g., "Vaseline®"), lanoline, polyethylene glycols, alcohols, transdermal enhancers, and combinations of two or more thereof.

In some embodiments, formulations suitable for topical application achieve transdermal delivery. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient.

Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration may also be delivered by iontophoresis (passage of a small electric current (~15 mA) to "inject" electrically charged ions into the skin) through the skin. For this, the dosage form typically takes the form of an optionally buffered aqueous solution of the active compound, i.e. a cysteinyl compound.

Formulations suitable for transdermal administration may also be delivered by using an infusion pump connected to a needle that is inserted through the skin, for example, those developed by Medtronic used to deliver insulin. Amounts of compound used in a transdermal device as described herein may vary, depending on many factors including the size of the device and its release characteristics, the amount of the pharmaceutical active agent and the estimated duration of action of the device. Broadly, amounts of compound typically range from about 0.1% to about 10% w/v.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose in accordance with the invention.

Parenterally administered compositions are formulated to allow for injection, either as a bolus or as a continuous infusion. For parenteral application, "parenteral" meaning subcutaneous injections, intravenous, intramuscular, intrasternal injection, or infusion techniques, particularly suitable vehicles consist of solutions, preferably oily or aqueous solutions, as well as suspensions, emulsions, or implants. Formulations for injection can be prepared in unit dosage forms, such as ampules, or in multi-dose units, with added preservatives. The compositions for injection can be in the form of suspensions, solutions, or emulsions, containing either oily or aqueous additives. They may also contain formulatory agents such as suspending agents, stabilizing agents, and/or dispersing agents. A cysteinyl compound may also be presented in powder form for reconstitution with a suitable vehicle before use.

The compositions of the present invention also may be in the form of a sterile injectable aqueous or oleaginous suspension. Injectable compositions, such as sterile injectable aqueous or oleaginous suspensions, may be formulated according to the known art using suitable dispersing or wetting agents and suspending agents. The sterile injectable composition may also be a sterile injectable solution or suspension in a nontoxic parenterally acceptable diluent or solvent, for example, as a solution in 1,3 butanediol. Among the acceptable vehicles and solvents that may be employed are water, Ringer's solution, and isotonic sodium chloride solution. In some embodiments, formulations of the present invention suitable for parenteral administration conveniently comprise sterile aqueous preparations of the active compound, i.e. a cysteinyl compound, which preparations are preferably isotonic with the blood of the intended recipient. Such preparations may conveniently be prepared by mixing the active compound with water or a glycine buffer and rendering the resulting solution sterile and isotonic with the blood.

In addition, sterile, fixed oils are conventionally employed as a solvent or suspending medium. Aqueous suspensions may contain substances which increase the viscosity of the suspension and include, for example, sodium carboxymethyl cellulose, sorbitol and/or dextran. Optionally, the suspension may also contain stabilizers.

Alternately, a compound of the present invention can be added to a parenteral lipid solution.

9. Combination Therapy

It is contemplated that a provided compound can be used in combination with other drugs or therapeutic agents.

In some embodiments of the present invention, the one or more described isoprenyl compound or complex thereof, or a composition comprising a compound or complex of the subject invention, can be administered in combination with one or more other therapeutically active agents. In some embodiments, active agents administered in combination are administered as part of a single composition; in some embodiments, active agents administered in combination are administered as separate compositions.

To give but a few examples, in some embodiments, a compound, complex, or composition of the subject invention is administered in combination with another agent.

In some embodiments, cysteinyl compounds as described herein are administered in combination with one or more other agents intended to treat the same condition, or disease. As used herein, additional therapeutic agents that are normally administered to treat a particular disease, or condition, are known as "appropriate for the disease, or condition, being treated."

In some embodiments, cysteinyl compounds of the present invention are administered in combination with one or more other pharmaceutically active agents intended to treat a different disease, disorder, or condition. For example, in some embodiments, it may be desirable to administer an inventive compound in order to reduce inflammation while concurrently administering a different pharmaceutically active agent in order to achieve a different biological result.

To give but one example, it is known that transdermal administration of pharmaceutically active agents often causes skin irritation at the site of delivery. Indeed, it is not uncommon that a skin irritating agent (e.g., SDS) be administered prior to or concurrent with application of a transdermal device such as, for example, a transdermal patch, in order to facilitate the delivery. Applicants have found that addition or co-administration of a cysteinyl compound as described herein in combination with transdermal administration of another pharmaceutically active agent can reduce inflammation and/or irritation associated with the transdermal administration of the other pharmaceutically active agent.

It is also known that single or chronic injections of a pharmaceutically active agent may sometimes result in inflammation, whether due to the identity of the pharmaceutically active agent (i.e., as an irritant) or to the mode of delivery. The present invention contemplates co-administration of one or more compounds of the present invention, in order to reduce inflammation associated with single or chronic injection of a pharmaceutically active agent.

Exemplary pharmaceutically active agents whose delivery, whether transdermally or by injection, may cause skin irritation include levadopa, pro-drug forms of levadopa, insulin, estradiol, estrogen, progesterone, progestins, progestogen, testosterone, nicotine, nitroglycerin, cholinesterase inhibitors, stimulants, antidepressants, and analgesics.

To give another example, application of certain agents such as, for example, hair relaxants, which commonly are or contain basic agents (e.g., NaOH), can cause skin irritation (e.g., irritation and/or inflammation of the scalp). According to the present invention, one or more cysteinyl compounds can be administered together with such a hair relaxant (or other agent) to reduce skin irritation and/or inflammation.

In some embodiments, described isoprenyl compounds or complexes are administered together with one or more other anti-inflammatory agents. Representative such anti-inflammatory agents include, for example, NSAIDs such as Acetominaphen (Tylenol), Aspirin, Celecoxib (Celebrex), Diclofenac (Voltaren), Diflunisal (Dolobid), Etodolac (Lodine), Ibuprofen (Motrin), Indomethacin (Indocin), Ketoprofen (Orudis), Ketorolac (Toradol), Nabumetone (Relafen), Naproxen (Aleve, Naprosyn), Oxaprozin (Daypro), Piroxicam (Feldene), Salsalate (Amigesic), Sulindac (Clinoril), Tolmetin (Tolectin), salicylic acid; and/or steroids such as glucocorticoids, for example, clobetasol (Clobex or Olux), dexamethasone, cortisol, testosterone, estrogen, estradiol, progesterone, etc.

In some embodiments, described isoprenyl compounds are administered together with one or more pain-relieving agents. Representative such pain relieving agents include, for example, NSAIDs such as Acetominaphen (Tylenol), Aspirin, Celecoxib (Celebrex), Diclofenac (Voltaren), Diflunisal (Dolobid), Etodolac (Lodine), Ibuprofen (Motrin), Indomethacin (Indocin), Ketoprofen (Orudis), Ketorolac (Toradol), Nabumetone (Relafen), Naproxen (Aleve, Naprosyn), Oxaprozin (Daypro), Piroxicam (Feldene), Salsalate (Amigesic), Sulindac (Clinoril), Tolmetin (Tolectin); and/or steroids such as glucocorticoids, for example, clobetasol (Clobex or Olux), dexamethasone, cortisol, testosterone, estrogen, estradiol, progesterone, etc. Alternatively or additionally, representative pain-relieving agents include, for example, articaine, benzocaine, bupivacaine, carticaine, chloroprocaine, cinchocaine/dibucaine, cocaine, cyclomethycaine, dimethyocaine/larocaine, etidocaine, levobupivacaine, lidocaine/lignocaine, mepvacaine, piperocaine, prilocalne, propoxycaine, procaine/novocaine, proparacaine, ropivacaine, saxitoxin, tetracaine/amethocaine, trimecaine, and/or combinations thereof.

In some embodiments, described isoprenyl compounds are administered together with glucocortocoids, aspirin, diclofenac, lidocaine, etc., and/or combinations thereof.

In some embodiments, described isoprenyl compounds are administered together with one or more other anti-bacterial agents. Representative such anti-bacterial agents include antibiotic agents such as penicillins, cephalosporins, carbacephems, cephamycins, carbapenems, monobactams, aminoglycosides, glycopeptides, quinolones, tetracyclines, macrolides, sulfonamides, fluoroquinolones, and lincosamides; and other anti-bacterial agents such as benzoyl peroxide and sulfur.

In some embodiments, described isoprenyl compounds are administered together with one or more keratolytic agents. Representative keratolytic agents include benzoyl peroxide, fluorouracil, resorcinol, salicylic acid, tretinoin, and the like.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

EXAMPLES

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all classes, subclasses and species of each of these compounds, disclosed herein.

The compounds utilized as starting materials may be synthesized according to methods known in the art or synthesized by the methods disclosed in Brown et al., "Prenylated Proteins. A Convenient Synthesis of Farnesyl Cysteinyl Thioethers, J. Am. Chem. Soc., 113, pp. 3176-3177 (1991), the disclosure of which is incorporated by reference herein.

The following general experimental procedures were used for Examples 1-7 as described below. Proton Nuclear Magnetic Resonance ($^1$HNMR) spectroscopy was recorded on a Bruker 500 MHz spectrometer, dimethyl sulfoxide (DMSO-d6), methanol (CD$_3$OD) or chloroform (CDCl$_3$) was used as $^1$H-NMR solvent. The residual proton absorption of the deuterated solvent was used as the internal standard. All $^1$H-NMR chemical shift are reported as δ values in the parts per million (ppm). The splitting pattern abbreviations are as follows: s, singlet; d, doublet; t, triplet; q, quartet; br, broad; m, multiplet; dd, doublet of doublet; dt, doublet of triplets. The HPLC analysis was done using a phenomenex luna C$_{18}$ (2)50×4.6 mm column. The mobile phase is 60% water, 40% acetonitrile containing 0.05% trifluoroacetic acid at 2 ml per minute flow rate for the first 2.5 minutes, followed by a gradient to 100% acetonitrile containing 0.05% TFA over 10 minutes. The eluent is observed at 214 nm.

Example 1

Synthesis of (4-((R)-1-carboxy-2-((2E,6E)-3,7,11-trimethyldodeca-2,6,10-trienylthio)ethylamino)-4-oxobutanoic acid) (Compound B)

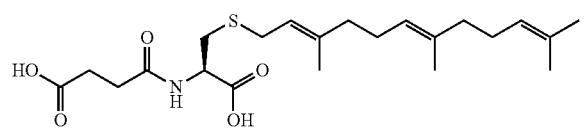

To a solution of 5-trans, trans-farnesyl-L-cysteine (500 mg, 1.54 mmol) in THF and first portion of K$_2$CO$_3$ (2 mmol) was cooled to 5° C. with vigorous stirring. To this stirred solution was added succinic anhydride (308 mg, 3.1 mmol) drop wise while maintaining the PH at 9-10 with another portion of K$_2$CO$_3$ (4 mmol). The mixture was stirred at room temperature for 2 h, HPLC analysis showed completion of the reaction. The pH of the reaction mixture then adjusted to 2 by the addition of 2N HCl solution. The acidic solution was extracted three times with 10 ml of ethyl acetate. The combined organic extract was washed with water, brine and dried over sodium sulfate, the solvent was removed on rotary evaporator to afford crude product, which was further purified by preparative HPLC (535 mg, 82% yield): $^1$H-NMR (500 MHz, CDCl$_3$) δ 1.59 (s, 6H), 1.66 (s, 6H), 2.05 (m, 8H), 2.60 (m, 2H), 2.48 (m, 2H), 2.86 (dd, 1H), 2.94 (dd, 1H), 3.10 (dd, 1H), 3.12 (dd, 1H), 4.68 (dd, 1H), 5.06 (m, 2H), 5.20 (t, 1H); $^{13}$C-NMR (125 MHz, CDCl$_3$) δ 16.0, 16.1, 17.7, 25.7, 26.5, 26.7, 29.4, 29.8, 30.5, 32.6, 39.6, 39.7, 52.2, 119.3, 123.8, 124.3, 131.3, 135.4, 140.3, 173.4, 174.2, 176.8; ES-MS: mass calcd for Chemical Formula: C$_{22}$H$_{35}$NO$_5$S 425.6 (M+). Found (M+Na) m/z 448.

Example 2

Synthesis of ((E)-4-((R)-1-carboxy-2-((2E,6E)-3,7,11-trimethyldodeca-2,6,10-trienylthio)ethylamino)-4-oxobut-2-enoic acid) (Compound A)

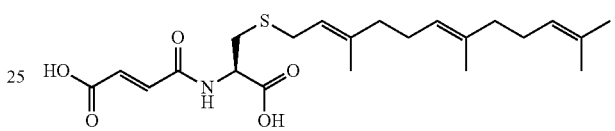

To a solution of S-trans, trans-farnesyl-L-cysteine (500 mg, 1.54 mmol) in THF and first portion of K$_2$CO$_3$ (3 mmol) was cooled to 5° C. with vigorous stirring. To this stirred solution was added maleic anhydride (302 mg, 3.07 mmol) portions wise while maintaining the PH at 9-10 with another portion of K$_2$CO$_3$ (3 mmol). The mixture was stirred at room temperature for 3 h, HPLC analysis showed completion of the reaction. The pH of the reaction mixture then adjusted to 2 by the addition of 2N HCl solution. The acidic solution was extracted three times with 15 ml of ethyl acetate. The combined organic extract was washed with water, brine and dried over sodium sulfate and then concentrated to afford crude product, which was further purified by preparative HPLC (552 mg, 85% yield): $^1$H-NMR (500 MHz, CD$_3$OD) δ 1.50 (bs, 6H), 1.57 (s, 3H), 1.59 (s, 3H), 1.85-2.10 (m, 8H), 2.68 (dd, J=6.5, 14.5, 1H), 2.95 (dd, J=4.5, 14.0 Hz, 1H), 3.07 (dd, J=7.0, 13.0 Hz, 1H), 3.17 (dd, J=8.5, 13.5 Hz, 1H), 4.59 (dd, J=4.5, 8.5), 4.97-5.02 (m, 2H), 5.12 (t, J=7.5, 1H), 6.21 (d, J=13.0 Hz, 1H), 6.47 (d, J=13.0 Hz, 1H); $^{13}$C-NMR (125 MHz, CDCl$_3$) δ 16.2, 16.3, 17.8, 25.3, 26.0, 27.4, 27.8, 30.3, 33.3, 40.8, 40.9, 54.0, 121.5, 125.1, 125.5, 132.1, 133.3, 134.4, 136.3, 140.7, 167.7, 168.0, 172.9; ES-MS: mass calcd for Chemical Formula: C$_{22}$H$_{33}$NO$_5$S 423.6 (M+). Found (M+Na) m/z 446.

Example 3

Synthesis of Synthesis of Monosodium 4-(R)-1-carboxy-2-((2E,6E)-3,7,11-trimethyldodeca-2,6,10-trienylthio)ethylamino)-4-oxobutanoate ("SFC-monosodium")

A solution of sodium hydroxide (90 mg, 2.26 mmol) in DI H$_2$O (1 mL) was prepared first and cooled down to room temperature. Then, a 50 mL RB flask equipped with stir bar was charged a solution of SFC (960 mg, 2.26 mmol) in methanol (5 mL). The sodium hydroxide aqueous solution was added dropwise. The mixture was stirred at room temperature for 10 minutes and pH of the mixture was 6.65. The solvent was removed in vacuo and dried under high vacuum overnight to yield the desired product (749 mg, 74% yield). $^1$H NMR (500 MHz, D$_2$O) δ 1.500 (s, 3H), 1.512 (s, 3H), 1.574 (s, 3H), 1.599 (s, 3H), 1.873-2.028 (m, 8H), 2.440-2.577 (m, 4H), 2.767 (dd, J=8.5, 14.0 Hz, 1H), 2.926 (dd, J=4.0, 14.0 Hz, 1H), 3.159 (d, J=7.5 Hz, 2H), 4.372 (dd, J=4.5, 8.0 Hz, 1H), 5.027-5.039 (m, 2H), 5.167 (t, J=7.5 Hz, 1H); $^{13}$C NMR (125 MHz, D$_2$O) δ 15.548, 15.579, 17.179, 25.172, 26.092, 26.334, 29.329, 30.901, 31.081, 33.149, 39.274, 39.338, 53.871, 119.513, 123.967, 124.400, 131.24, 135.166, 139.796, 174.147, 176.472, 178.645; ES-MS: mass calcd for Chemical Formula: C$_{22}$H$_{34}$NNaO$_5$S 447.56. Found (M+1) m/z 448.20.

Example 4

Synthesis of Synthesis of Disodium 4-(R)-1-carboxy-2-((2E,6E)-3,7,11-trimethyldodeca-2,6,10-trienylthio)ethylamino)-4-oxobutanoate ("SFC-disodium")

A solution of sodium hydroxide (1.885 g, 47.126 mmol) in DI H$_2$O (5 mL) and methanol (20 mL) was prepared. Then, a 250 mL RB flask equipped with stir bar was charged a solution of SFC (10.014 g, 23.563 mmol) in methanol (20 mL) and the sodium hydroxide solution. The mixture was stirred at room temperature for 10 minutes. The solvent was removed in vacuo and dried under high vacuum overnight to give the desired product (11.01 g, 99.6% yield). $^1$H NMR (500 MHz, D$_2$O) δ 1.551 (s, 6H), 1.608 (s, 3H), 1.621 (s, 3H), 1.935-1.964 (m, 2H), 2.012-2.111 (m, 6H), 2.377-2.420 (m, 2H), 2.451-2.494 (m, 2H), 2.755 (dd, J=8.0, 13.5 Hz, 1H), 2.912 (dd, J=5.0, 14.0 Hz, 1H), 3.178 (d, J=8.0 Hz, 2H), 4.312 (dd, J=4.5, 7.5 Hz, 1H), 5.127 (dd, J=7.0, 13.5 Hz, 2H), 5.210 (t, J=7.5 Hz, 1H); $^{13}$C NMR (125 MHz, D$_2$O) δ 15.151, 15.268, 16.919, 24.811, 25.333, 25.680, 28.918, 32.247, 32.888, 38.704, 38.736, 54.319, 119.555, 124.071, 124.378, 133.246, 136.385, 140.445, 174.991, 177.066, 181.033; ES-MS: mass calcd for Chemical Formula: C$_{22}$H$_{33}$NNa$_2$O$_5$S 469.55 Found (M−Na+H+1) m/z 448.20; Anal. Calcd for C$_{22}$H$_{35}$NNa$_2$O$_6$S (SFC-disodium salt mono hydrate) C, 54.20; H, 7.24; N, 2.87; S, 6.58. Found: C, 54.51; H, 7.40; N, 2.84; S, 6.50.

Biological Examples

Described below are in vivo assays used to measure the biological activity of provided compounds, including the anti-inflammatory properties of the compounds, as measured by edema inhibition, erythema inhibition and MPO inhibition.

Example 5

Mouse Model of Inflammation-Edema, Erythema and MPO Background

The mouse ear model of contact irritation has been established as an appropriate model to determine whether topically applied anti-inflammatories inhibit the development of acute, chemically induced dermal irritation [see Van Arman, C. G. et al., *Anti-inflammatory Drugs*, Clin. Pharmacol. Ther. 16, 900-4 (1974); Young et al., *Tachyphylaxis in 12-Otetradecanoylphorbolacetate- and Arachidonic Acid-Induced Ear Edema*; J. Invest. Dermatol. 80:48-52, (1983); Tramposch et al., *In Vivo Models of Inflammation*, (Morgan D W, Marshall L A eds), Birkhaüser Verlag: Basel, pp 179-204, 1999; and Gordon et al., *Topical N-Acetyl-S-Farnesyl-L-Cysteine Inhibits Mouse Skin Inflammation, and Unlike Dexamethasone, Its Effects Are Restricted to the Application Site*, J. Invest. Dermatol., 128(3):643-54, 2008 March)]. Moreover, the mouse ear model has been used by various groups to identify and compare members of differing classes of anti-inflammatory agents with multiple mechanisms of action (reviewed in Tramposch et al., 1999, supra). The commonly used end points of inflammation are edema (Young et al., 1983, supra), (assayed by increase in ear thickness), neutrophil infiltration (which is measured by assaying for the neutrophil marker myeloperoxidase ("MPO") (see Bradley et al., *Cellular and Extracellular Myeloperoxidase in Pyogenic Inflammation*, Blood, 60(3):618-22; 1982) and erythema (skin redness). Using this model, we investigated the in vivo anti-inflammatory activity of S-isoprenyl and S-farnesyl cysteine compounds to identify which structures possess physical or chemical properties critical for inhibiting innate inflammation in the skin.

(a) Protocol—Edema Inhibition

The protocol for inducing in vivo acute contact inflammation on the ears of live mice has been described elsewhere (reviewed in Tramposch, 1999, supra). In brief, mice were sedated and their ears were treated with 1.2 μg/20 uL TPA (i.e., tetradecanoylphorbol-13-acetate). After 5 minutes, we dosed these TPA-treated ears with a single 8 μg/20 uL dose, a 2 ug/20 uL dose, or both doses, of the S-isoprenyl and S-farnesyl compounds. After 24 hours, the mice were sacrificed and edema was measured by taking micrometer readings of each ear. The percent inhibition of edema was determined by taking the average ear thickness of compound-treated ears and dividing it by the average thickness of 12 ears that only received TPA and subtracting that value from 100%. These values were corrected for the thickness of normal, non TPA-treated mouse ears of littermate controls. Results demonstrating percent inhibition of edema for representative compounds of the present invention are depicted in FIG. 1. ED$_{50}$ values were calculated as described in Gordon et al., "Topical N-acetyl-5-farnesyl-L-cysteine Inhibits Mouse Skin Inflammation, and Unlike Dexamethasone, its Effects Are Restricted to the Application Site", J. Invest. Derm., Vol. 128 pp. 643-654 (2008). ED$_{50}$ results for AFC and Compounds A and B are depicted in FIG. 2.

(b) Protocol-Erythema Inhibition

Another well documented biomarker of skin inflammation is skin redness, termed erythema, which is caused by capillary congestion and dilation in response to various chemical and environmental insults (see Denig, N. I. et al., *Irritant Contact Dermatitis. Clues to Causes, Clinical Characteristics, and Control*, Postgrad Med., May (1998); 103(5):199-200, 207-8, 212-3). The protocol for measuring erythema inhibition by S-isoprenyl and 5-farnesyl cysteine compounds was developed in-house by utilizing the CR-400 chroma meter from Konica Minolta (http://www.konicaminolta.com/instruments/products/color/colorimeters/cr400-410/index.html). This instrument was used to measure the Δa* redness value from 6 mm biopsy punches taken 24 hours post TPA/compound treatment as described in the edema inhibition section above. The percent inhibition of erythema was determined by taking the average Δa* redness value of compound-treated ears and dividing it by the average Δa* value of 12 ears that only received TPA and subtracting that value from 100%. These values were corrected for the Δa* value of non TPA-treated mouse ears of littermate controls. Results demonstrating percent inhibition of erythema for representative compounds of the present invention are depicted in FIG. 1. Gordon et al., "Topical N-acetyl-5-farnesyl-L-cysteine Inhibits Mouse Skin Inflammation, and Unlike Dexamethasone, its Effects Are Restricted to the Application Site", J. Invest.

Derm., Vol. 128 pp. 643-654 (2008). $ED_{50}$ results for AFC and Compounds A and B are depicted in FIG. 2.

(c) Protocol-MPO Inhibition

To assay for inhibition of dermal neutrophil infiltration by S-isoprenyl and 5-farnesyl cysteine compounds, a standard method was used (see Bradley et al., 1982, supra; Young et al., 1983, supra; De Young et al, "Edema and Cell Infiltration in the Phorbol Ester-treated Mouse Ear are Temporally Separate and can be Differentially Modulated by Pharmacologic Agents", Agents Actions, 26(3-4): 335-41 (March 1989); and Rao et al. (1993) *Comparative Evaluation of Arachidonic Acid (AA)- and Tetradecanoylphorbol Acetate (TPA)-Induced Dermal Inflammation*, Inflammation 17:723-41). Briefly, we homogenized 6 mm biopsy punches taken from both compound-treated ears as well as TPA-treated and non-treated control groups. We quantitated the levels of MPO by a colorimetric reaction that was measured spectrophotometrically. The percent inhibition of neutrophil infiltration by each S-isoprenyl and 5-farnesyl cysteine compound was determined by comparing the average MPO levels in the presence and absence of these compounds. The calculation for percent inhibition of MPO was determined similar to that as described for calculating the percent edema inhibition, see the Edema Inhibition protocol, supra. Results demonstrating percent inhibition of MPO for representative compounds of the present invention are depicted in FIG. 1. Gordon et al., "Topical N-acetyl-5-farnesyl-L-cysteine Inhibits Mouse Skin Inflammation, and Unlike Dexamethasone, its Effects Are Restricted to the Application Site", J. Invest. Derm., Vol. 128 pp. 643-654 (2008). $ED_{50}$ results for AFC and Compounds A and B are depicted in FIG. 2.

(d) Inhibition of *Propionibacterium acnes* Growth

The present example demonstrates that certain SFC compounds of the present invention exhibit superior or similar anti-bacterial activity when compared to benzoyl peroxide, a well-known anti-bacterial and anti-acne agent. The assay for the inhibition of growth of *Propionibacterium acnes* bacteria was described elsewhere (Nakatsuji et al., J Invest Dermatol, 2009, 129: 2480-2488). In brief, the strain ATCC 6919 of *P. acnes* (American Type Culture Collection, Manassas, Va.) was cultured on *Brucella* agar (RO1254, Remel, Lenexa, Kans.) supplemented with 5% (v/v) defibrinated sheep blood, vitamin K (5 mg/ml, Remel, Lenexa, Kans.), and hemin (50 mg/ml, Remel, Lenexa, Kans.), under an anaerobic condition using Gas-Pak (BD, Sparks, Md.) at 37° C. A single colony was inoculated in Reinforced *Clostridium* Medium (Oxford, Hampshire, England) and cultured at 37° C. under the anaerobic condition. Each of the inventive compounds A, B, C, D, E, F, G, H and I were dissolved in 100% (v/v) DMSO. Samples of each inventive compound and a solution of benzoyl peroxide ("BPO") were then each incubated with an inoculum of *P. acnes* at a concentration of $1 \times 10^6$ CFU per mL in Reinforced *Clostridium* Medium in a 96-well microplate (100 μL per well) under anaerobic conditions for 72 hours. Samples of each inventive compound were tested at final concentrations per well of 0.25 μg/mL, 0.5 μg/mL, 1.0 μg/mL, 1.95 μg/mL, 3.9 μg/mL, 7.8 μg/mL, 15.625 μg/mL, 31.25 μg/mL, 62.5 μg/mL, 125 μg/mL, 250 μg/mL, and 500 μg/mL. A control well received only 5% (v/v) of DMSO in place of a sample of an inventive compound. After 72 hours incubation under anaerobic conditions, the *P. acnes* cultures in the 96-well microplate were mixed well and then absorbance readings at 600 nm were taken to determine bacterial growth. *P. acnes* growth curves was plotted and the concentration of each inventive SFC compound tested that yielded 50% inhibition of bacterial growth (IC50) was determined using SigmaPlot. IC50 results demonstrating the effect of inventive compounds on inhibition of *P. acnes* growth for compounds A and B are depicted in FIG. 1.

(e) Determination of Minimum Bactericidal Concentration

The present example demonstrates that certain SFC compounds of the present invention exhibit anti-bacterial activity and exhibit low minimum bactericidal concentrations. The Minimal Bactericidal Concentration ("MBC") of the inventive compounds against *P. acnes* was determined using the following method. Sample solutions of an inventive compounds, for example, AFC and compound A, dissolved in 100% (v/v) DMSO, were each incubated with an inoculum of *P. acnes* at a concentration of $1 \times 10^7$ CFU/mL in a 96-well microplate with a total culture of 100 μl per well under anaerobic conditions, to yield final compound concentrations per well of 1 μg/mL, 5 μg/mL, 10 μg/mL, 25 μg/mL, 50 μg/mL, 100 μg/mL and 200 μg/mL. A control well received only 5% (v/v) of DMSO in place of the test solution of inventive compound. Following 5 hours of incubation, the reaction mixture was serially ($1:10$-$1:10^6$) diluted with PBS. The MBC was determined by inoculating the diluted culture (5 μl) onto a *brucella* agar plate (RO1254, Remel, Lenexa, Kans.). 72 hours after inoculation, colonies on the plates were counted, CFUs (Colony Forming Units) were calculated and the data was plotted by using SigmaPlot. The bacterial concentration (CFU/mL) of *P. acnes*, obtained with different concentrations of AFC (panel A) and compound A (panel B) to determine the MBC of each compound are depicted in FIG. 3.

(f) *P. acnes*-Induced Mouse Ear Model of Inflammation—MPO Endpoint

The methods for a model of *P. acnes-inflammation* are described elsewhere (Nakatsuji et al., J Invest Dermatol, 2008, 128: 2451-2457). Using this mouse in vivo model for *P. acnes*-induced inflammation, the present example demonstrates that certain SFC compounds of the present invention, when topically applied to a site of inflammation induced by bacterial challenge exhibit in vivo anti-inflammatory activity, as evidenced by the effect on the commonly-used inflammatory end-points such as neutrophil infiltration (MPO neutrophil marker). Using this mouse in vivo model for *P. acnes*-inflammation, the present example further demonstrates that certain SFC compounds of the present invention, when topically applied to a site of inflammation induced by bacterial challenge, for example by *P. acnes* exhibit in vivo anti-inflammatory activity, as evidenced by the effect on the commonly-used inflammatory end-points such as neutrophil infiltration (MPO neutrophil marker), and are therefore useful as anti-acne agents. [00210] The protocol for inducing inflammation using *P. acnes* bacterial challenge on the mouse ear was slightly modified from the method described previously (Natatsuji et al., 2008). Briefly, Swiss Webster (ICR, 6-8 weeks old) mouse ears were injected with living *P. acnes* culture intradermally. An amount of 20 μl aliquots of living *P. acnes* (ATCC 6919, $3 \times 10^6$ CFU) suspended in PBS was intradermally injected in the central portion of the ear. As a control, 20 μl of PBS was injected into control animals. Significant cutaneous erythema, ear swelling (edema), and granulomatous response (MPO activity) were observed in *P. acnes-injected* ear 24 hours after the bacterial injection, but not induced by phosphate-buffered saline (PBS) injection. [00211] To assay for inhibition of dermal neutrophil infiltration by SFC compounds, a standard method was used (see Bradley et al., J Invest Dermatol, 1982, 78: 206-209; Young et al., J Invest Dermatol, 1983, 80: 48-52; De Young et al, Agents Actions, 1989, 26: 335-41; and Rao et al., Inflammation, 1993, 17: 723-41). Briefly, 6 mm biopsy punches taken from both compound-treated ears as well as non-treated control ears were homogenized in 400 µl of 0.5% hexadecyltrimethylammonium bromide in 50 mM potassium phosphate buffer (pH 6.0) using the Fast Prep 24 (MP Biomedicals, Solon, Ohio). Supernatants were assayed for MPO activity using a model EL 340 96-well plate reader (BioTek Instruments, Winooski, Vt.). The percent inhibition of neutrophil infiltration by each SFC compound was determined by comparing the average MPO levels in the presence and absence of these compounds. The percent inhibition of MPO was determined by taking the average MPO activity of compound-treated ears and dividing it by the average MPO activity of 12 ears that only received the *P. acnes* challenge and subtracting that value from 100%. These values were corrected for the MPO activity of normal, non *P. acnes*-treated mouse ears of littermate controls. Summary of MPO activity ranges determined from an MPO activity assay for dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), and compound A (administered at a dose of 0.8 mg/20 µL).

(g) *P. acnes*-Induced Mouse Ear Model of Inflammation—Cytokine Release

The protocol for inducing acute inflammation in mouse ears using *P. acnes* has been described elsewhere (Nakatsuji et al., J Invest Dermatol, 2008, 128: 2451-2457) and similar to the protocol described in Example 10. Using this mouse in vivo model for contact irritation, the present example demonstrates that certain inventive compounds, when topically applied, exhibit in vivo anti-inflammatory activities at sites of inflammation induced by *P. acnes*, in part, by inhibiting the levels of pro-inflammatory cytokines, such as IL-6, TNF-α, IL-8 and IL-1β, resulting in the observed effects on the inflammatory end-point of neutrophil infiltration (MPO neutrophil marker), as demonstrated in Example 10. The present example therefore demonstrates that certain inventive compounds are useful for treating bacterial induced inflammation and are therefore useful as anti-acne agents. [00213] The protocol for inducing inflammation using *P. acnes* bacterial challenge on the mouse ear was slightly modified from the method described previously (Natatsuji et al., 2008). Briefly, Swiss Webster (ICR, 6-8 weeks old) mouse ears were injected with living *P. acnes* (strain ATCC 6919) culture intradermally. An amount of 20 µl aliquots of living *P. acnes* (ATCC 6919, 3×106 CFU) suspended in PBS was intradermally injected in the central portion of the ear. As a control, 20 µl of PBS was injected into control animals. Significant cutaneous erythema, ear swelling (edema), and granulomatous response (MPO activity) were observed in *P. acnes-injected* ear 24 hours after the bacterial injection, but not induced by phosphate-buffered saline (PBS) injection. Ear tissue biopsies (6 mm), taken from both compound-treated ears and non-treated control ears were obtained and homogenized using a Fast Prep 24 (MP Biomedicals, Solon, Ohio) for two cycles of 45 seconds with Lysing Matrix A in mammalian extraction buffer (Pierce) with protease inhibitors cocktail (Roche). Supernatants were assayed by enzyme-linked immunosorbent assays (ELISA) for the stimulated release of IL-6, TNF-α, IL-8, and IL-1β, using appropriate protein standards (BD Pharmigen). [00214] Summary of cytokine activity ranges determined with dexamethasone (administered at a dose of 1.6 mg/20 µL), clobetasol (administered at a dose of 0.1 mg/20 µL), salicylic acid (administered at a dose of 0.4 mg/20 µL), AFC (administered at a dose of 0.8 mg/20 µL), and compound A (administered at a dose of 0.8 mg/20 µL).

(h) LPS-TLR4-Induced Inflammation Model in HMEC-1 Cells—Inhibition of Cytokine levels The activation of Toll-like receptor 4 (TLR4) by lipopolysaccharide (LPS), a common class of bacterial endotoxin, induces the release of proinflammatory cytokines that are necessary to mediate key immune and inflammatory responses (reviewed in Yong-Chen et al., Cytokines, 2008, 42: 145-151). The present example demonstrates that certain SFC compounds of the present invention inhibit TLR4 inflammatory signaling pathways resulting in reduction of proinflammatory cytokine release, for example of IL-8. Human Microvascular Endothelial cells (HMECs) were cultured in EC basal medium (EBM; Cambrex, Walkersville, Md.), supplemented with 0.5% fetal bovine serum (FBS), epidermal growth factor (EGF) (10 ng/mL) hydrocortisone (1 µg/mL) and 100 U/mL penicillin/100 µg/mL streptomycin at 37° C. with 5% $CO_2$ (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of 0.25×106 cells/well in supplemented media in 12-well plates. After cells were allowed to adhere (6-8 hours), media was changed to depleted media. After 24 hours, depleted media was removed and fresh depleted media containing various concentrations of SFC and Compound A in triplicate were added to the appropriate wells. Two hours later, to induce a pro-inflammatory response, LPS was added (100 µM) in separate wells (in triplicate) (Bender et al., Exp Dermatol, 2008, 17: 752-60; and Seiffert et al., J Invest Dermatol, 2006, 126: 1017-27). Cell cultures were examined for viability by Trypan blue exclusion and the reduction of 3-(4, 5-dimethylthiazol-2-yl)-5-(3-carboxymethoxyphenyl)-2-(4-sulfophenyl)-2H-tetrazolium (MTS assay; Promega, Madison, Wis.) to determine the percentage of viable cells of various treatment concentrations of SFC and Compound A. After 6 hours of incubation, supernatants were harvested and assayed by enzyme-linked immunosorbent assays (ELISA) for the stimulated release of IL-8 using appropriate protein standards (BD Pharmigen). IL-8 levels (pg/mL), obtained with AFC and Compound A using an LPS-TLR4-induced inflammation model in HMEC-1 cells were determined (i) ATPγS-Purinergic Receptor-Induced Inflammation Model in HMEC-1 Cells—Inhibition of Cytokine Levels Bacterial challenges, particularly on the epithelial surfaces, have been show to trigger the release of extracellular signaling nucleotide molecules, such as ATP. ATP, serving as an extra-cellular signaling molecule, is known to activate purinergic P2 receptors which are expressed on a variety of cells involved in immune and inflammatory responses, including macro- and microvascular endothelial cells (ECs). During the pathophysiology of such epithelial-related disorders, dermal microvascular ECs recruit inflammatory cells, including leukocytes, to the sites of bacterial challenge, such as on the skin, triggered, in part, by the release of proinflammatory mediators, such as IL-6, IL-8, Groα and MCP-1 (Swerlick et al., J Invest Dermatol, 1993, 100: 111S-115S). It has been previously demonstrated that the non-hydrolyzable analog of ATP, i.e., ATPγS induces the production of proinflammatory cytokines in human dermal microcascular endothelial cells through the modulation of the P2 purinergic receptor signaling (Seiffert et al., J Invest Dermatol, 2006, 126: 1017-27). [00217] The protocol for inducing the production of proinflammatory cytokines in human microvascular endothelial cells (HMECs) with ATPγS, as previously described, serves as a cell-based model for studying the anti-inflammatory activities of test compounds. Using this cell-based model, the present example demonstrates that certain SFC compounds of the present invention exhibit anti-inflammatory activity, as evidenced by the inhibition of ATPγS-induced-purinergic receptor-mediated release of proinflammatory mediators such as IL-8 and MCP-1. Briefly, HMECs were cultured in EC basal medium (EBM; Cambrex, Walkersville, Md.), supplemented with 0.5% fetal bovine serum (FBS), epidermal growth factor (EGF) (10 ng/mL) hydrocortisone (1 μg/mL) and 100 U/mL penicillin/100 μg/mL streptomycin at 37° C. with 5% CO2 (referred to as supplemented media). In order to avoid possible immunomodulating effects of these agents during agonist/antagonist treatments, for some periods, cells were kept in EBM supplemented only with 0.5% FBS and penicillin/streptomycin without EGF or hydrocortisone (referred to as depleted media). Cells were plated at a concentration of 0.25×106 cells/well in supplemented media in 12-well plates. After cells are allowed to adhere (6-8 hours), media is changed to depleted media. After 24 hours, depleted media was removed and fresh depleted media containing various concentrations of SIG989 in triplicate was added to the appropriate wells. Two hours later, to induce a pro-inflammatory response, ATPγS was added (100 μM) in separate wells (in triplicate) (Bender et al., Exp Dermatol, 2008, 17: 752-60; and Seiffert et al., J Invest Dermatol, 2006, 126: 1017-27). Cell cultures were examined for viability by Trypan blue exclusion and the reduction of 3-(4,5-dimethylthiazol-2-yl)-5-(3-carboxymethoxyphenyl)-2¬ (4-sulfophenyl)-2H-tetrazolium (MTS assay; Promega, Madison, Wis.) to determine the percentage of viable cells of various treatment concentrations of SIG989. After 6 hours of incubation, supernatants were harvested and assayed by enzyme-linked immunosorbent assays (ELISA) for the stimulated release of MCP-1, and IL-8 using appropriate protein standards (BD Pharmigen). IL-8 levels (pg/mL), obtained with AFC and Compound A using an ATPγS-purinergic Receptor-induced Inflammation model in HMEC-1 cells were determined MCP-1 levels (pg/mL), obtained with AFC and Compound A using an ATPγS-purinergic Receptor-induced Inflammation model in HMEC-1 cells were also determined Equivalents Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A compound having the formula:

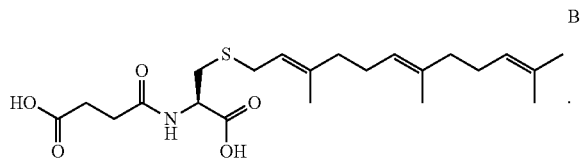 [SMILES: CC(C)=CCC/C(C)=C/CC/C(C)=C/CSC[C@H](NC(=O)CCC(=O)O)C(=O)O ; "."]

2. A composition comprising the compound of claim 1 and a binding partner, wherein the compound of claim 1 is complexed with the binding partner.

3. The composition of claim 2, wherein said binding partner is a monosodium salt.

4. The composition of claim 2, wherein said binding partner is a disodium salt.

5. A composition comprising a compound according to claim 1, and a pharmaceutically acceptable adjuvant, carrier, or vehicle.

6. The composition of claim 5, wherein said composition is formulated for topical administration.

7. A method for treating or lessening the severity of an epithelial condition or disorder in a patient in need thereof, wherein said condition or disorder is selected from the group consisting of: skin edema, skin erythema, *propionibacterium acnes* growth, and inflammation produced by *propionibacterium acnes* growth, said method comprising the step of administering to said patient a compound of claim 1 or a composition comprising the compound of claim 1.

8. The method of claim 7, wherein the method comprises inhibiting or reducing sensory irritation, itch, erythema, edema or vesiculation.

9. The method of claim 7, wherein the epithelial disorder or condition is caused or aggravated by bacteria.

10. The method of claim 7, wherein the condition or disorder is selected from cellulitis; erysipelas; impetigo; ecthyma; ecthyma gangrenosum; hidradenitis; cutaneous anthrax; necroticizing fasciitis; toe web infections; sycosis barbae; furuncles and carbuncles; Staphylococcal scalded skin syndrome; blistering distal dactylitis; acute paronychia; folliculitis; acne vulgaris; cutaneous diphtheria; erythrasma; and bacterial colonization of open wounds.

11. The method of claim 9, wherein the epithelial condition or disorder is selected from the group consisting of acne vulgaris and rosacea.

12. A compound having the formula:

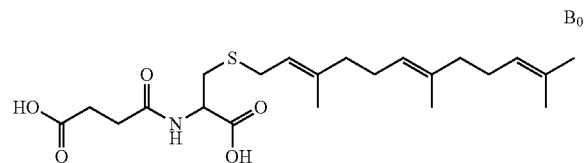 [SMILES: CC(C)=CCC/C(C)=C/CC/C(C)=C/CSCC(NC(=O)CCC(=O)O)C(=O)O]

or a pharmaceutically acceptable salt thereof.

* * * * *